United States Patent
Rahman et al.

(10) Patent No.: US 12,318,185 B2
(45) Date of Patent: Jun. 3, 2025

(54) BREATHING MEASUREMENT AND MANAGEMENT USING AN ELECTRONIC DEVICE

(71) Applicant: SAMSUNG ELECTRONICS CO., LTD., Gyeonggi-Do (KR)

(72) Inventors: Md Mahbubur Rahman, San Jose, CA (US); Bashima Islam, Champaign, IL (US); Tousif Ahmed, San Jose, CA (US); Nathan Robert Folkman, San Francisco, CA (US); Anh Minh Dinh, San Francisco, CA (US); Sean Bornheimer, San Francisco, CA (US); Ebrahim Nematihosseinabadi, Santa Clara, CA (US); Jilong Kuang, San Jose, CA (US); Jun Gao, Menlo Park, CA (US)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 254 days.

(21) Appl. No.: 17/406,086

(22) Filed: Aug. 19, 2021

(65) Prior Publication Data

US 2022/0054039 A1    Feb. 24, 2022

Related U.S. Application Data

(60) Provisional application No. 63/068,324, filed on Aug. 20, 2020.

(51) Int. Cl.
*A61B 5/08* (2006.01)
*A61B 5/00* (2006.01)

(52) U.S. Cl.
CPC .............. *A61B 5/08* (2013.01); *A61B 5/7267* (2013.01); *A61B 5/7405* (2013.01); *A61B 5/742* (2013.01); *A61B 2562/0204* (2013.01)

(58) Field of Classification Search
CPC ....... A61B 5/08; A61B 5/7267; A61B 5/0816; A61B 7/003; A61B 5/7405; A61B 5/742; A61B 2562/0204
See application file for complete search history.

(56) References Cited

U.S. PATENT DOCUMENTS

| 10,736,515 B2 | 8/2020 | Stoian et al. |
| 2017/0273617 A1 | 9/2017 | Kaji |

(Continued)

FOREIGN PATENT DOCUMENTS

| CN | 109998487 A | 7/2019 |
| JP | 2022055805 A | 4/2022 |

(Continued)

OTHER PUBLICATIONS

WIPO Application No. PCT/KR2021/011135, International Search Report, Nov. 26, 2021, 3 pg.

(Continued)

*Primary Examiner* — Matthew Kremer
*Assistant Examiner* — Evelyn Grace Park
(74) *Attorney, Agent, or Firm* — CUENOT, FORSYTHE & KIM, LLC

(57) ABSTRACT

Passively monitoring a user's breathing with a device can include identifying breathing modes of the user's breathing and responsive to detecting a trigger mode based on the identifying, generating an instruction adapted to the trigger mode. The instruction can be conveyed to the user via the device. The monitoring can include determining phases of the user's breathing with the device. Determining the phases can include receiving acoustic signals generated by an acoustic sensor in response to a user's breathing and generating acoustic data comprising features extracted from the acoustic signals. Phases of the user's breathing can be determined by classifying the acoustic data using a machine (Continued)

learning model trained based on signal processing of motion signals generated by a motion sensor in response to human breathing motions. Though trained using signal processing of motion signals, the machine learning model is trained to classify acoustic data.

18 Claims, 14 Drawing Sheets

(56) References Cited

U.S. PATENT DOCUMENTS

| | | | |
|---|---|---|---|
| 2018/0338705 A1 | 11/2018 | Konishi et al. | |
| 2019/0029563 A1 | 1/2019 | Sels et al. | |
| 2019/0038179 A1* | 2/2019 | Tanriover | A61B 5/0803 |
| 2020/0008708 A1 | 1/2020 | Tan et al. | |
| 2020/0297955 A1 | 9/2020 | Shouldice | |
| 2020/0329979 A1 | 10/2020 | Shantharam | |
| 2021/0150873 A1* | 5/2021 | Shouldice | A61B 5/7228 |

FOREIGN PATENT DOCUMENTS

| | | | |
|---|---|---|---|
| KR | 20200139023 A | 12/2020 | |
| WO | 2012155257 A1 | 11/2012 | |
| WO | 2019179836 A1 | 9/2019 | |
| WO | 2019229543 A1 | 12/2019 | |
| WO | 2020220142 A1 | 11/2020 | |

OTHER PUBLICATIONS

WIPO Application No. PCT/KR2021/011135, Written Opinion, Nov. 26, 2021, 4 pg.

"Breath Track: Detecting Regular Breathing Phases from Unannotated Acoustic Data Captured by a Smartphone," May 2021, 20 pg.

* cited by examiner

BREATHING MEASUREMENT AND MANAGEMENT USING AN ELECTRONIC DEVICE

CROSS-REFERENCE TO RELATED APPLICATIONS

This application claims the benefit of U.S. Provisional Patent Application No. 63/068,324 filed on Aug. 20, 2020, which is incorporated herein by reference in its entirety.

TECHNICAL FIELD

This disclosure relates to detecting and measuring physiological phenomena and, more particularly, to measuring and analyzing human breathing using an electronic device.

BACKGROUND

Various health conditions can be linked to an individual's breathing. Whether as a symptom or cause of an underlying pulmonary or other physical condition, a breathing anomaly can stem from a serious health challenge such as lung cancer, emphysema, chronic obstructive pulmonary disease (COPD), viral or bacterial infection, or other respiratory disease. Even an otherwise healthy individual may suffer from poor breathing habits such as shallow breathing or mouth breathing. Poor breathing habits can contribute to physiological problems such as high blood pressure, elevated heart rate, and reduced physical strength or mental acuity by disrupting an individual's oxygen-carbon dioxide balance. Even psychological conditions such as anxiety, stress, and anger can affect the individual's breathing. Breathing difficulties also are associated with sleep disorders, including sleep apnea.

Not surprisingly, therefore, detecting and monitoring an individual's breathing patterns can be a critical component for diagnosing and treating a variety of health-related conditions. Detecting and monitoring an individual's breathing patterns can even help the individual develop more healthful breathing, which can relieve stress, improve sleep, or otherwise enhance the individual's overall health.

SUMMARY

In an example implementation, a computer-based method for monitoring a user's breathing with a device can include passively monitoring the user's breathing with a device during a predetermined time interval generating sensor-generated signals, wherein the sensor-generated signals include at least one of acoustic signals or motion signals. The method also can include identifying one or more breathing modes of the user's breathing by processing data created from the sensor-generated signals using a machine learning model. Responsive to detecting a trigger mode based on the identifying, the method can include generating an instruction adapted to the trigger mode and conveying the instruction to the user via the device.

In another example implementation, a system for monitoring a user's breathing with a device includes a processor configured to initiate operations. The operations can include passively monitoring the user's breathing with a device during a predetermined time interval generating sensor-generated signals, wherein the sensor-generated signals include at least one of acoustic signals or motion signals. The operations also can include identifying one or more breathing modes of the user's breathing by processing data created from the sensor-generated signals using a machine learning model. Responsive to detecting a trigger mode based on the identifying, the operations can include generating an instruction adapted to the trigger mode and conveying the instruction to the user via the device.

In another example implementation, a computer program product includes one or more computer readable storage media, and program instructions collectively stored on the one or more computer readable storage media. The program instructions are executable by computer hardware to initiate operations. The operations can include passively monitoring the user's breathing with a device during a predetermined time interval generating sensor-generated signals, wherein the sensor-generated signals include at least one of acoustic signals or motion signals. The operations also can include identifying one or more breathing modes of the user's breathing by processing data created from the sensor-generated signals using a machine learning model. Responsive to detecting a trigger mode based on the identifying, the operations can include generating an instruction adapted to the trigger mode and conveying the instruction to the user via the device.

This Summary section is provided merely to introduce certain concepts and not to identify any key or essential features of the claimed subject matter. Other features of the inventive arrangements will be apparent from the accompanying drawings and from the following detailed description.

BRIEF DESCRIPTION OF THE DRAWINGS

The inventive arrangements are illustrated by way of example in the accompanying drawings. The drawings, however, should not be construed to be limiting of the inventive arrangements to only the particular implementations shown. Various aspects and advantages will become apparent upon review of the following detailed description and upon reference to the drawings.

DETAILED DESCRIPTION

Figure 1:
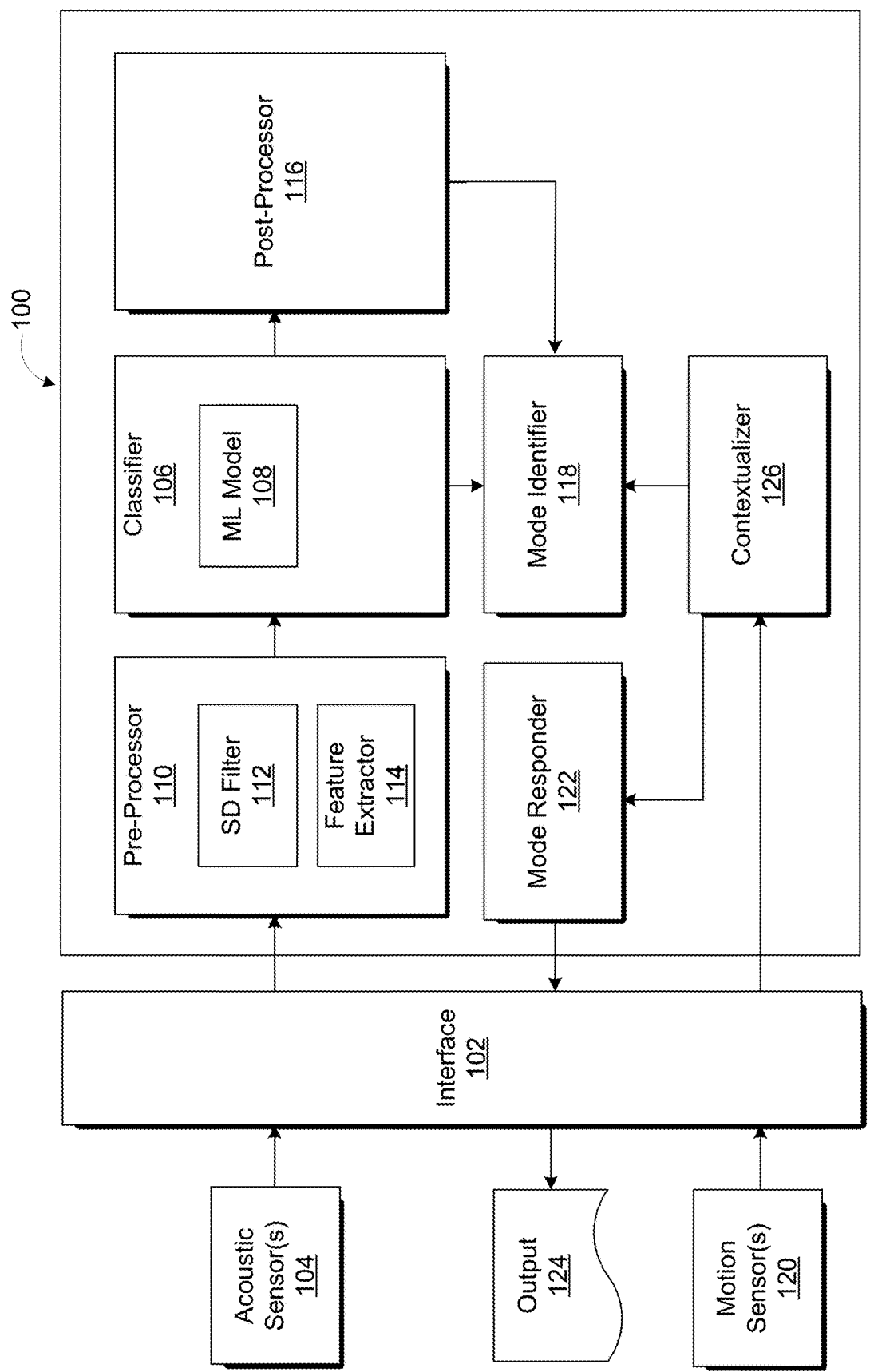
FIG. 1 illustrates an example breathing monitoring system configured to determine breathing phases of a user.

While the disclosure concludes with claims defining novel features, it is believed that the various features described herein will be better understood from a consideration of the description in conjunction with the drawings. The process(es), machine(s), manufacture(s) and any variations thereof described within this disclosure are provided for purposes of illustration. Any specific structural and functional details described are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

This disclosure relates to detecting and measuring physiological phenomena and, more particularly, to measuring and analyzing human breathing using an electronic device. Measuring and analyzing an individual's breathing can be a critical aspect of diagnosis and treatment of several respiratory conditions. Even for healthy individuals, there can be situations in which monitoring and analyzing the individual's breathing can be beneficial. Poor breathing can have surprisingly negative effects. Shallow breathing, for example, can raise the blood pressure, elevate the heart rate, and disrupt the oxygen-carbon dioxide balance of an individual, reducing the user's mental acuity or physical strength. Mouth breathing is another mode of breathing associated with health problems like high blood pressure, poor sleep, sleep apnea, snoring, gum disease, halitosis, increased stress, decreased productivity, and even facial deformities. Frequently an individual is not even aware of engaging in improper breathing. An individual may develop poor breathing habits that if undetected can go unchecked without the individual realizing their negative effects on the individual's overall health.

An individual who typically enjoys healthy breathing may nonetheless have reasons for self-monitoring breathing. Assessing the effects of the individual's exercise regime can be based on a breathing assessment before and after exercise. An individual may wish to monitor and manage breathing when the individual is under stress, anxious, or otherwise facing an atypical situation that can affect the individual's breathing. Nevertheless, the ability to monitor and manage one's own breathing using a device, especially one that is portable, that is convenient to use but accurate.

An aspect of the systems, methods, and computer program products disclosed herein is detecting breathing modes reflecting physiological events based on determining an individual's breathing phases based on acoustic data. The acoustic data can be conveniently captured using a portable device such as earbuds or a smartphone. The device can passively monitor the user's breathing patterns, breathing habits, and/or heart rate, and determine an appropriate moment for the user to change the mode of breathing or perform mindful breathing. While monitoring the user's breathing, the device singly or in combination with one or more other devices can manage the user's breathing by providing real-time, personalized biofeedback.

Another aspect is identifying trigger modes of breathing by the user. The identifying can be based on acoustic data and/or motion data. The data can be created from sensor-based signals generated by one or more device sensors. In certain arrangements disclosed herein, the user's breathing can be passively monitored with a device during a predetermined time interval. One or more device sensors can generate sensor-generated signals. The sensor-generated signals can include acoustic signals and/or motion signals. One or more breathing modes of the user's breathing can be identified by processing data created from the sensor-generated signals using a machine learning model.

In response to identifying a trigger mode of breathing, a nudge is conveyed to the user, via the device, the nudge prompting or instructing the user to engage in mindful breathing. As defined herein, a "trigger mode" is a breathing mode that is associated with an adverse health effect. Examples of a trigger mode include shallow breathing and mouth breathing or sympathetic nervous system excitation including psychosocial stress. A "nudge" is defined herein as a notification, instruction, or other audible or visual message that is conveyed to the user by a device in response to detecting a trigger mode. A nudge can make a user aware of an irregular or unhealthy breathing pattern. A nudge can provide an explicit instruction instructing the user to undertake a specific type of mindful breathing in a prescribed manner to correct unhealthy breathing. "Mindful breathing" is defined herein as controlled breathing consciously performed in a predetermined manner by the user.

Another aspect is detecting breathing modes reflecting physiological events, the breathing modes detected from the breathing phases determined based on acoustic data. The proper timing for generating and conveying a breathing nudge also can be determined from the user's breathing phases in real-time. Moreover, acoustic data can be combined with motion data in assessing breathing conditions and events associated with the user. Still another aspect is determining breathing phases (i.e., inhalation, exhalation) using machine learning. A machine learning model, as disclosed herein, may be trained according to a novel teacher-student architecture. In accordance with the architecture, a machine learning model (e.g., convolutional neural network) is trained using signal processing, the signal processing performed on sensor-generated motion data. Though trained through signal processing, once trained the machine learning model is operative on acoustic data and based on the acoustic data can classify a user's breathing phases in real-time. The acoustic data can be created from acoustic signals captured with a portable device (e.g., earbuds, smartphone). The unique teacher-student architecture disclosed herein not only obviates the need for manual annotation of machine learning training data, but moreover significantly enhances the accuracy of the machine learning model.

Further aspects of the embodiments described within this disclosure are described in greater detail with reference to the figures below. For purposes of simplicity and clarity of illustration, elements shown in the figures have not necessarily been drawn to scale. For example, the dimensions of some of the elements may be exaggerated relative to other elements for clarity. Further, where considered appropriate, reference numbers are repeated among the figures to indicate corresponding, analogous, or like features.

FIG. 1 illustrates example breathing monitoring and management system (system) 100. System 100 can be implemented in hardware (e.g., dedicated circuitry), software (e.g., processor-executable code), or a combination thereof. In certain arrangements, system 100 is implemented in a portable device (e.g., earbuds, smartphone, smartwatch), such as portable device 1000 described with respect to FIG. 10 which can be worn or comfortably carried by a user. The portable device can implement the operative features of system 100 operating singly or cooperatively with another device communicatively linked via a wired or wireless connection with the portable device.

Illustratively, system 100 operatively couples with one or more acoustic sensors 104 via interface 102 of the device in which system 100 is implemented. Interface 102 can comprise interface circuitry (e.g., interface circuitry 1006 in FIG. 10) coupled with other circuitry (e.g., processors 1004 in FIG. 10) of the device in which system 100 is implemented. Acoustic sensor(s) 104, in accordance with certain embodiments, can comprise an IMU embedded in an earbud worn by the user or embedded in a smartphone carried by a user. In yet other embodiments, acoustic sensor(s) are embedded in one device that is communicatively coupled with another device in which system 100 is implemented. In still other embodiments, system 100 is implemented in other types of devices that include interface 102 via which system 100 operatively couples with acoustic sensor(s) 104.

System 100 illustratively includes classifier 106, which implements machine learning (ML) model 108. Classifier 106 can determine phases of the user's breathing by classifying acoustic data using ML model 108. The acoustic data can comprise features extracted from acoustic signals generated by acoustic sensor(s) 104 and received with the device (e.g., earbuds, smartphone) in which system 100 is implemented. ML model 108 is trained based on signal processing of motion signals generated by a motion sensor in response to human breathing motions. Once trained, however, ML model 108 can classify acoustic data created from acoustic signals.

Optionally, system 100 can include pre-processor 110, which pre-processes acoustic signals received from acoustic sensor(s) 104. Pre-processor 110 comprises sound discriminating (SD) filter 112 and feature extractor 114. SD filter 112 operates as a type of admission control gate by differentiating between breathing sounds and non-breathing sounds carried by the acoustic signals. Feature extractor 114 extracts breathing-related features from the acoustic signals filtered by SD filter 112. The output of pre-processor 110 passes from pre-processor 110 to classifier 106.

System 100 optionally can include post-processor 116 for processing the output of classifier 106. Post-processor 116 enhances classifier 106's accuracy in classifying the phases of the user's breathing by eliminating classifications that are likely anomalous.

Illustratively, system 100 also includes mode identifier 118, which is capable of identifying different modes of the user's breathing. Mode identifier 118 can identify different modes of the user's breathing based on the breathing phases determined by classifier 106, which can enhance the accuracy with which mode identifier 118 identifies breathing modes. Mode identifier 118, however, is also capable of identifying different modes of the user's breathing independently of the breathing phases by extracting data pertaining to the user's breathing characteristics directly from acoustic and/or motion signals. The data can be extracted from signals generated, for example, by a head-worn device such a pair of earbuds, smart glasses, or virtual reality device. The breathing modes identified include certain trigger modes, and system 100 can optionally include mode responder 122 that responds to identification of trigger modes of breathing. Mode responder 122 can respond to a trigger mode by conveying output 124 to the user, which provides a nudge correlated with the specific trigger mode identified by mode identifier 118. The nudge can indicate the specific trigger mode identified and/or can instruct the user to undertake mindful breathing specifically selected by mode responder 122 to correct the user's current mode of breathing. Optionally, system 100 also includes contextualizer 126, which provides a context of the user's breathing and can be used in selecting the nudge that is conveyed to the user by mode responder 122 to correct a breathing mode given a current context of the user's breathing. As described in detail below, contexts identified by contextualizer 126 can include physiological, psychological, and social contexts associated with the user.

Classifier 106 is capable of determining the user's breathing phases in real-time based solely on acoustic data created from acoustic signals generated by and received via interface 102 from acoustic sensor(s) 104. Classifier 106 creates the acoustic data using one or more predetermined features extracted from the acoustic signals, e.g., by feature extractor 114, structuring the acoustic data for input to machine learning (ML) model 108. The extracted features can include, for example, mel-frequency cepstral coefficients (MFCCs), log spectrograms, and/or other breathing-related features described herein. The acoustic data created by classifier 106 can be structured as tensors—data structures (e.g., vectors, matrices, or higher dimensional structures) whose elements are the features extracted from the acoustic signals generated by acoustic sensor(s) 104.

Classifier 106 determines distinct phases of a user's breathing according to classification of the acoustic data by ML model 108. ML model 108 is trained to classify acoustic data according to a teacher-student architecture. In accordance with the specific teacher-student architecture disclosed herein, a teacher model processes signals generated by motion sensors and, based on the signal processing of motion signals, teaches the student model (ML model 108) to classify breathing phases based on acoustic data. Thus, once trained ML model 108, though learning from motion data created from signal processing, classifies breathing phases at runtime solely based on acoustic data.

ML model 108 can be implemented in a deep learning neural network. In some embodiments, ML model 108 is a convolutional neural network (CNN). In one embodiment, ML model 108 is implemented in a CNN that is trained to classify the user's breathing based on tensors (e.g., 40×22 matrices) whose features comprise normalized MFCCs extracted from acoustic signals captured by acoustic sensor(s) and using MFCC bands having a hop length of 256. With an audio sampling rate of 11.2 kHz, classifier 106 can create 40×22 feature matrices, based on which ML model 108 as a CNN classifies the user's breathing phases. Classifier 106, in other embodiments, can implement one or more different ML models, can use additional or alternative features extracted from the acoustic signals, and/or can create data structures comprising differently dimensioned tensors (e.g., vectors, matrices, or higher dimensional tensors).

Figure 2A:
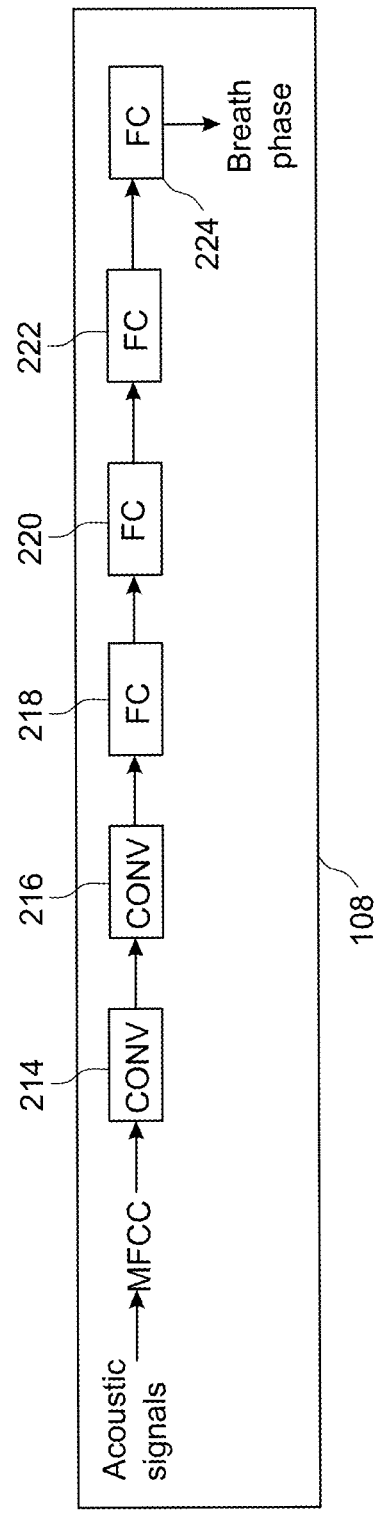
FIGS. 2A and 2B illustrate an example implementation and a teacher-student architecture for training a machine learning model implemented by the system of FIG. 1.
Figure 2B:
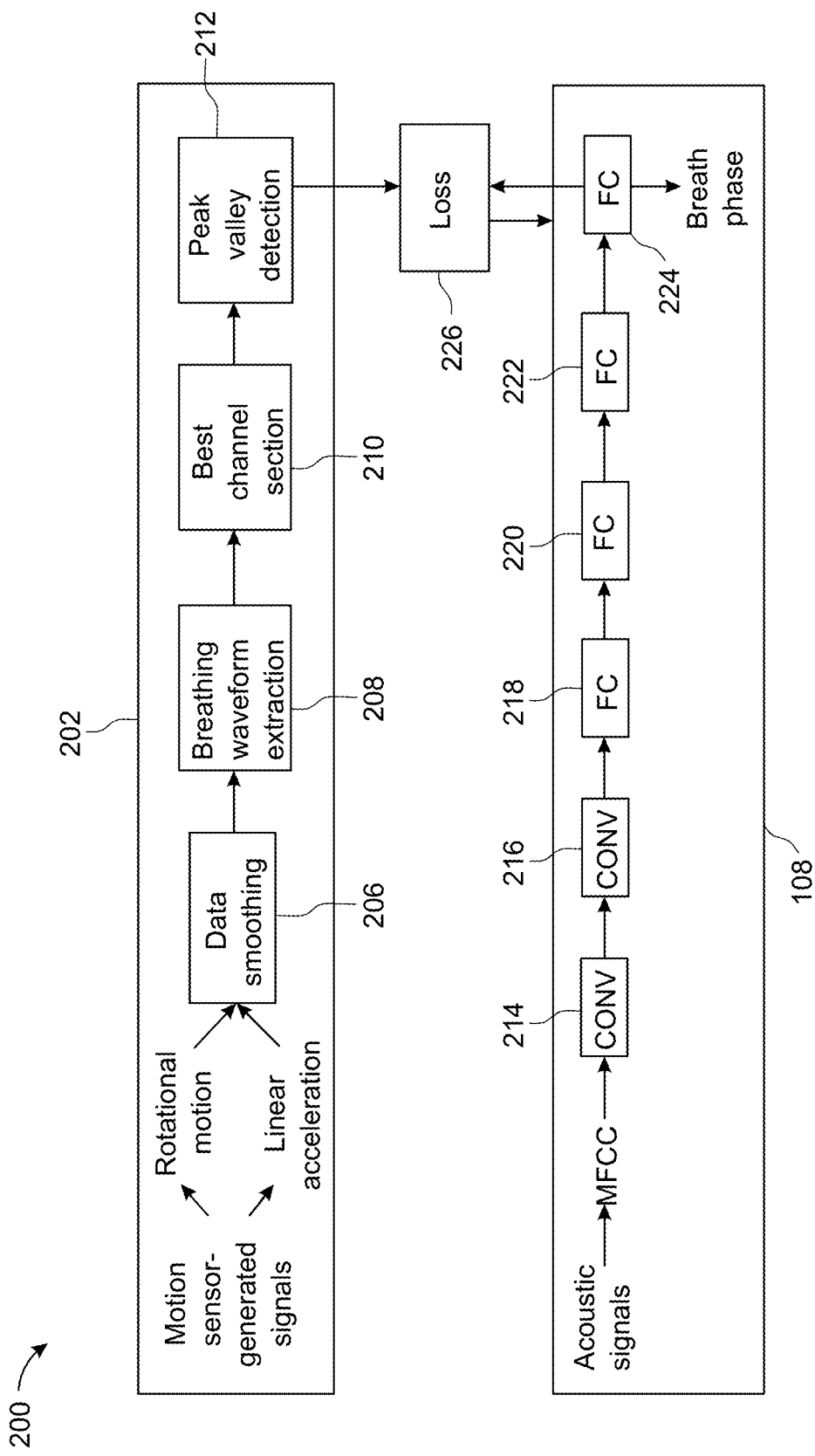

Referring additionally to FIGS. 2A and 2B, an example implementation and training of ML model 108 as a CNN is illustrated. FIG. 2A illustrates a specific example implementation of ML model 108 as a CNN deep learning model. Illustratively, ML model 108 includes convolution layers 214 and 216; fully connected intermediate layers 218, 220, and 222; and fully connected output layer 224. Convolution layers 214 and 216 each comprises four filters, which are implemented as 2×2×1 tensors. The activation function of each of convolution layers 214 and 216 is the rectified linear unit (ReLU) activation function. Fully connected intermediate layers 218, 220, and 222, respectively, comprise 500, 200, and 50 units. The activation function of each of fully connected intermediate layers 218, 220, and 222 is the ReLU activation function. The activation function of fully connected output layer 224 is the sigmoid activation function. In other embodiments, ML model 108 can comprise a different number of convolution and/or intermediate layers, each with a different number of units and using the same or different activation functions.

ML model 108 is trained using teacher-student architecture 200, as illustrated in FIG. 2B. In accordance with the teacher-student architecture, teacher model 202 performs signal processing, and student model (ML model 108) learns to classify breathing phases based on the signal processing output generated by teacher model 202. The input to teacher model 202 comprises sensor-generated motion signals. In certain embodiments, the motion sensor-generated signals are generated by one or more IMUs embedded in a device (e.g., smartphone), which can be held against a subject's chest.

IMU-generated signals that are input to teacher model 202, for example, can comprise 3-axis linear acceleration and 3-axis rotational motion signals. Illustratively, module 206 of teacher model 202 performs smoothing on the 3-axis linear acceleration and 3-axis rotational motion signals. Module 208 extracts breathing waveforms based on the output of module 206. Module 210 is capable of selecting a best axis or channel from the multi-channel data received from block 208. In one arrangement, module 210 selects the best axis or channel using a 6-axis (3-axis accelerometer and 3-axis gyroscope) algorithm, which can select the best axis or channel based on the maximum periodicity in the signal waveform derived using Fourier transformation. Module 212 is capable of estimating respiration cycles from waveforms generated from the signals received over the axis or channel selected by module 210. Module 212, in one arrangement, estimates the respiration cycle by applying a Savitzky-Golay filter and detecting waveform peaks and valleys corresponding to the expansion and contraction of the subject's chest as the subject is breathing. Teacher model 202 accurately identifies the phases of the subject's breathing by post processing the selected data stream. In one arrangement, a post processor (not shown) applies a Kalman filter, or linear quadratic estimator, to the selected data stream to identify the phases of the user's breathing based on motion data.

Operatively, teacher model 202 of teacher-student architecture 200 is capable of providing supervised training to the student model (ML model 108), enabling the student model to leverage the knowledge domain of teacher model 202. Teacher model 202 receives input comprising sensor-generated motion signals (e.g., generated by a device IMU), generated in response to breathing motions (e.g., chest expansion and contraction) of a subject whose breathing is monitored over a predetermined interval. Teacher model 202 outputs the phases of a subject's breathing determined based on signal processing of the signals generated in response to the subject's breathing. In certain arrangements, teacher model 202's determinations are based on 500 ms breathing segments consisting of both inhalation and exhalation phases. Teacher model 202 chooses the phase that takes the majority of the duration and labels training examples accordingly. As the student model (ML model 108) is trained, the student model classifies the breathing phases of the training examples in response to acoustic data based on the subject's breathing. The classifications of breathing phases based on examples correctly annotated (labeled) by teacher model 202 and corresponding classifications made by the student model (ML model 108) are input to the loss function 226, which calculates the loss based on differences between teacher model 202's correctly determined labels and the student's classification. That is, loss function 226 compares each labeled output of teacher model 202 with the classification made by the student model of the identical breathing segment. Motion signals and acoustic signals can be time-aligned. In one embodiment, loss function 226 is implemented as a binary cross-entropy loss function. Other loss functions can be used in other embodiments. The parameters of student model 204 are iteratively refined until the classification made by the student model (ML model 108) achieves an acceptable accuracy level, which can be determined using a separate testing set data.

To date a nearly insurmountable challenge to training a ML model to distinguish among distinct breathing phases using acoustic data is an inability to annotate acoustic data due to the inaudible boundaries of breathing phases. A feature engineer attempting to manually annotate acoustic-based training data and listening to a subject's breathing encounters pauses between inhalation and exhalation phases. Such pauses, however, are non-existent in actual breathing. Pauses at the boundaries of breathing phase are inaudible to a human listener (e.g., feature engineer). An individual may pause at the boundary of a breath phase during controlled breathing (e.g., performing breathing exercises), but natural breathing typically does not involve holding one's breath or pausing one's breathing, making the entire phase of the individual's inhalation or exhalation inaudible to the human ear. Thus, annotation of acoustic signals based on audible sounds is not accurate, at least with respect to natural, regular breathing.

By contrast, in accordance with the teacher-student architecture disclosed herein, the ML model is trained using motion data created from waveforms of signals generated by motion sensors in response the individual's body movements during breathing. Sensor-generated motion data used for training the ML model is not tainted by artificial pauses—inaudible or otherwise—the way that acoustic data is. With the teacher-student architecture disclosed herein, a ML model implemented by classifier 106, although able to determine phases of the user's breathing based on the acoustic data, is in fact trained using sensor-generated motion data.

Training an ML model in accordance with teacher-student architecture 200, using motion data, overcomes the inherent limitations of acoustic data due to the inaudible boundaries of breathing phases. Using ML to classify motion data as with traditional architectures, however, poses its own challenges. Signals generated by a motion sensor are often corrupted with noise and tend to drift over time. The reliability of manual annotations based on unprocessed signals generated by an IMU or other type of motion-sensor is thus significantly diminished. Moreover, with respect to data based specifically on IMU-generated signals there arises the need to identify the best channel. An IMU typically provides six-channel data (3-axis accelerometer and 3-axis gyroscope). One channel generates signal responses representing the pattern of a user's breathing. Which channel provides the best representation depends on the orientation of the IMU. Finding the best channel manually during manual annotation is infeasible. Moreover, the low sampling rate of many IMUs typically fails to provide enough data to effectively train a deep learning neural network or other ML model.

These challenges are overcome by teacher-student architecture 200, in which ML model 108 is trained as a student that learns from signal processing performed by the teacher model. Based on the signal processing, ML model 108 learns to classify acoustic signals. Thus, a teacher-student architecture, in accordance with arrangements disclosed herein, not only eliminates the need for manual annotation, but also improves the performance of a ML model by transferring to a student model the knowledge gained through signal processing performed by the teacher model.

Figure 3A:
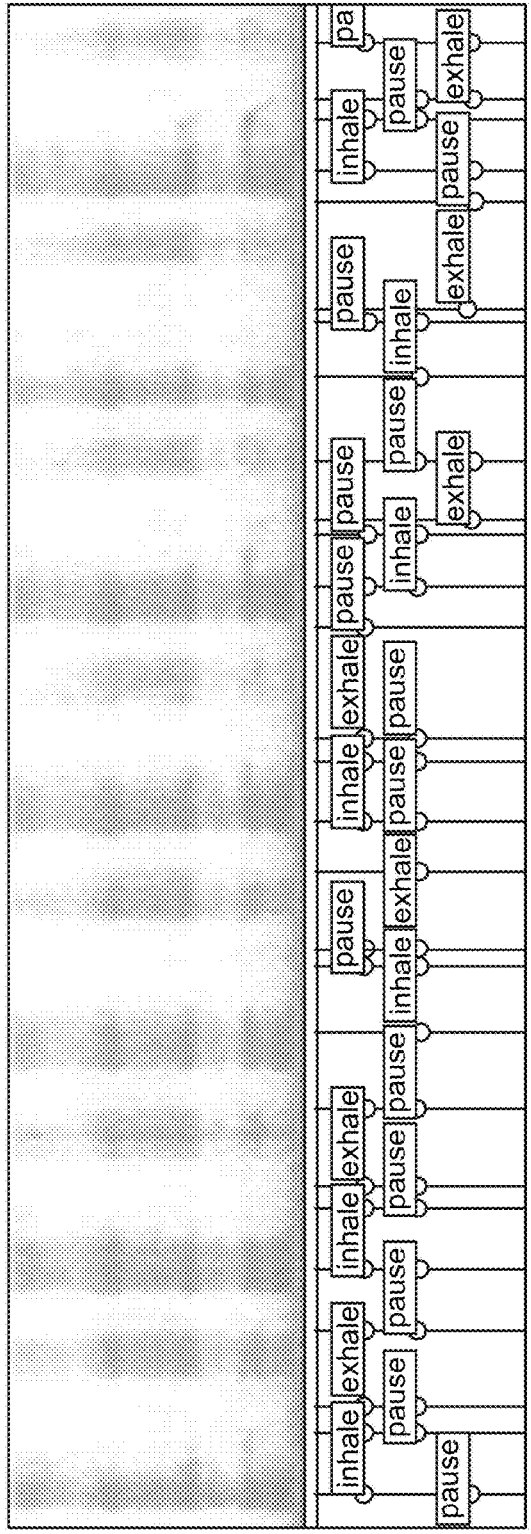
FIGS. 3A and 3B are example graphs, respectively, of acoustic signals and motion waveforms corresponding to an individual's breathing.
Figure 3B:
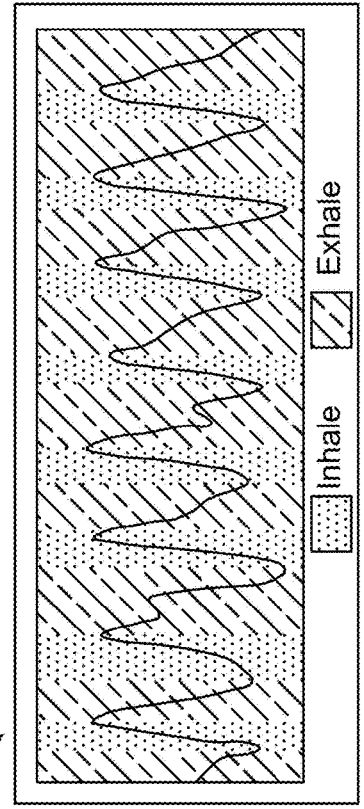

ML model 108 can be trained using data created from sensor-generated inhale and exhale signals collected from multiple subjects. Breathing characteristics of healthy subjects typically vary from those of pulmonary patients, such as with respect to breath duration. Thus, in certain arrangements, the multiple subjects include both pulmonary patients and healthy individuals, thereby enabling ML model 108 to learn the multiple subjects' acoustic signature variability based on the features of the acoustic data. FIGS. 3A and 3B provide, respectively, the time-domain spectrogram analysis of inhales and exhales based on acoustic data and a waveform of corresponding motion data. Note that the inhalation duration is smaller than the exhalation duration. This distinct acoustic signature allows us to classify the breathing phase. The variability learned through ML reflects variation in the frequency distribution of inhalation and exhalation phases; exhalation phases typically have a higher mean amplitude than do inhalation phases. The average energy of inhalation and exhalation phases is 19.08 dB and 69.76 dB, respectively. The signal-to-noise ratio (SNR) of inhalation and exhalation phases are −44.98 dB and −36.12 dB, respectively. The SNR and energy measurements also reflect lower amplitude in the inhalation phase.

The phases of an individual's breathing can be affected by various factors, including pulmonary ailments of various types. Thus, using a population comprising both pulmonary patients and healthy individuals to generate training examples from which ML model 108 learns to distinguish healthy breathing patterns from those associated with one or more adverse breathing conditions (e.g., COPD, viral infection).

In other arrangements, ML model 108 can be trained using data created from sensor-generated inhale and exhale signals collected specifically from the user of a device in which system 100 is implemented. Trained using data collected specifically from the user, ML model 108 provides a personalized or user-calibrated ML model. Training ML model 108 based on data collected from the user can be used in several ways. For example, system 100 can be used to monitor the user's breathing and detect when that breathing is in some respect deviating from an established norm. If the user is performing certain physical exercises, for example, system 100 can be used to determine whether the user is breathing properly while exercising. Accordingly, ML model 108 can be trained using user-specific data to detect deviations from a predetermined norm.

In some embodiments, generating training data by monitoring one or more subject's breathing and using the training data to ML model 108 can be performed using separate devices. For example, multiple subjects' breathing can be monitored using various monitoring devices and the resulting data processed by a computing node such as computing node 1000 described in the context of FIG. 10. ML model 108, once trained, can be downloaded from the computing node (e.g., cloud-based server) to a user device (e.g., earbuds, smartphone, smartwatch). ML model 108 can be trained to run on a mobile device, whereby the model is trained using clinical data generated with a device such as a spirometer.

Once trained based on data derived from signal processing, ML model 108 implemented by classifier 106 classifies phases of a user's breathing based on acoustic data in real-time.

Input to ML model 108 is acoustic data created from features (e.g., MFCC, log spectrogram) extracted from acoustic signals. Optionally, features are extracted by feature extractor 114 of pre-processor 110. Prior to extraction of features, the acoustic signals can be passed through one or more signal processing filters, such as optional SD filter 112 for separating non-breathing noises from breathing sounds carried by the acoustic signals. SD filter 112 in certain arrangements can comprise a second-order Butterworth high-pass filter and a Savitzky-Golay filter, which mitigate or eliminate background noise and unwanted frequencies. In certain arrangements, acoustic feature extractor 114 segments each one-minute filtered signal into thirty 500 ms frames and extracts acoustic features from each frame. In certain arrangements, the features extracted by feature extractor 114 include MFCC, extracted from MFCC bands having a hop length of 256. With an audio sampling rate of 11.2 k Hz, feature extractor 114 can create a 40×22 output feature matrix (described above), which can be used for non-breathing sound filtering and as input into classifier 106 (also described above). In other arrangements, other acoustic features can be extracted from the acoustic signals by acoustic feature extractor 114, including for example the log spectrogram, which yields similar output to that generated in response to MFCCs.

Non-breathing sounds are numerous and varied, including, for example, single and multi-person speech, vehicle and other machine-generated noises, a host of ambient noises, and other non-breathing sounds. SD filter 112 filters the various sounds, which would otherwise obscure or suppress breathing sounds. In some arrangements, SD filter 112 uses MFCC features to distinguish breathing sounds from non-breathing sounds. In other arrangements, SD filter 112 uses other acoustic features, such as log spectrogram to distinguish between breathing and non-breathing sounds. In certain arrangements, pre-processor 110 uses a random forest classifier of the principal components of the MFCC features to differentiate breathing and non-breathing sounds. An audio segment classified as breathing is retained for processing. An audio segment classified as non-breathing sounds is discarded. Pre-processor 110 can use majority voting in deciding whether each audio signal (e.g., one-minute segment) corresponds to the user's breathing or not.

Output of classifier 106 is optionally processed by post-processor 116, which exploits the sequential relation and temporal characteristics of the breathing phases among consecutive segments of the user's breathing to smooth the output by eliminating classifications that are likely anomalous. This smoothing as optionally performed by post-processor 116 thus enhances the accuracy of classifier 106's determination of the phases of the user's breathing.

Although enhancing the dynamic duration of breathing phases, performing classifications based on a 500 ms segmentation of the user's breathing (as described above) hinders the classifying of the lowest breathing phase duration. In certain embodiments, post-processor 116 is configured to analyze training data to learn the minimal exhalation and inhalation phase duration and use the domain knowledge to process output generated by classifier 106. Post-processor 116 smooths the output by identifying a misclassification of breathing segments based on classification of neighboring segments. Post-processor 116 identifies a miscalculation by detecting an anomalous inhale among exhale phases or anomalous exhale among inhale phases, detecting the anomaly by observing a neighboring segments' phase classification. Post-processor 116 rectifies an anomalous classification by reversing the classification. That is, given the binary nature of the classification and alternating nature of the breathing phases, upon detecting an anomalous classification, post-processor 116's smoothing changes an anomalous inhalation classification to exhalation and an anomalous exhalation classification to inhalation.

Mode identifier 118, as described above, can identify different modes of the user's breathing based on the breathing phases determined by classifier 106. Phase detection can enhance the accuracy of mode identification by mode identifier 118. As already described above, however, mode identifier 118 is also capable of identifying different modes of the user's breathing independently of the breathing phases by extracting data pertaining to the user's breathing characteristics directly from acoustic and/or motion signals. In certain embodiments, mode identifier 118 implements a ML model that is trained to distinguish among modes (e.g., shallow breathing, mouth breathing) based on various types of acoustic and/or motion features. Acoustic features can include, for example, energy and/or other aspects of the acoustic signals. Thus, in some embodiments, mode identifier 118 can distinguish among different modes based on energy distribution at different frequencies, which exhibit differences depending on the mode (e.g., lower frequency sounds exhibit different resonance patterns).

An ML model implemented by mode identifier 118 can be, for example, a deep learning model such as a CNN, a recurrent neural network (RNN), or the like. The ML model can be trained specifically for the user using training examples generated by monitoring the user's breathing. Based on the training examples, the ML model can learn certain baseline modes of the user's breathing. For example, while the user performs one or more prescribed breathing exercises, the ML model can automatically learn the baseline of the user's breathing depth as the user is passively breathing while sedentary and/or performing one or more routine activities.

In some embodiments, features used by the ML model implemented by mode identifier 118 include features extracted from signals generated by one or more motion sensors 120. For example, with system 100 implemented in a pair of earbuds worn by the user, the motion signals can be obtained from one or both IMUs embedded in the earbuds. The expansion and contraction of the user's lungs due to breathing also move the user's torso and head, and an earbud IMU captures the torso and head motion due to the user's breathing. Mode identifier 118 is capable of extracting feature signals generated by motion sensor(s) 120 in response to the user's torso and head motion. The features can be used by the ML model implemented by mode identifier 118 to identify modes of the user's breathing. In some embodiments, feature input (e.g., tensors, matrices, vectors) to the ML model implemented by mode identifier 118 is extracted from both acoustic and motion signals generated, respectively, by acoustic sensors 102 and motion sensor(s) 120.

Shallow breathing is an example breathing mode that is recognized by mode identifier 118 and identified as a trigger mode. Shallow breathing can affect the user's blood pressure and/or heart rate, and also can disrupt the user's oxygen-carbon dioxide balance, thereby reducing the user's mental acuity or physical strength.

Mode identifier 118 can identify the user's shallow breathing based on movement of the user's torso and head sensed by motion sensor(s) 120. With system 100 implemented in earbuds worn by the user, for example, the motion sensor can be IMUs embedded in the earbuds. Mode identifier 118, using a ML model that has learned the baseline of the user's breathing depth, can detect shallow breathing by comparing the user's current breathing depth with the user's ML model-determined baseline. In certain embodiments, mode identifier 118 determines that the user's breathing is shallow if the depth is less than a predetermined threshold (e.g., fifty percent) of the user's baseline breathing depth.

In other embodiments, mode identifier 118 detects the user's shallow breathing based on acoustic energy generated by the user's breathing. Acoustic features extracted from acoustic signals generated by acoustic sensor(s) 104 in response to the user's breathing can include acoustic energy. Mode identifier 118 can distinguish normal breathing from shallow breathing, which exhibits relatively lower energy compared to deep breathing, from acoustic energy features extracted from the acoustic signals captured by acoustic sensor(s) 104. In still other embodiments, mode identifier 118 determines shallow breathing of the user based on both acoustic energy and depth of the user's breathing determined by motion data. As described in greater detail below, the user's breathing depth can be extracted from motion data created, for example, from IMU or other motion sensor signals generated in response to head motion of the user induced by breathing. Mode identifier 118 can distinguish head motion induced by the user's breathing (e.g., muscle movement due to breathing) from non-breathing head motion (e.g., left or right head movement).

Figure 4B:
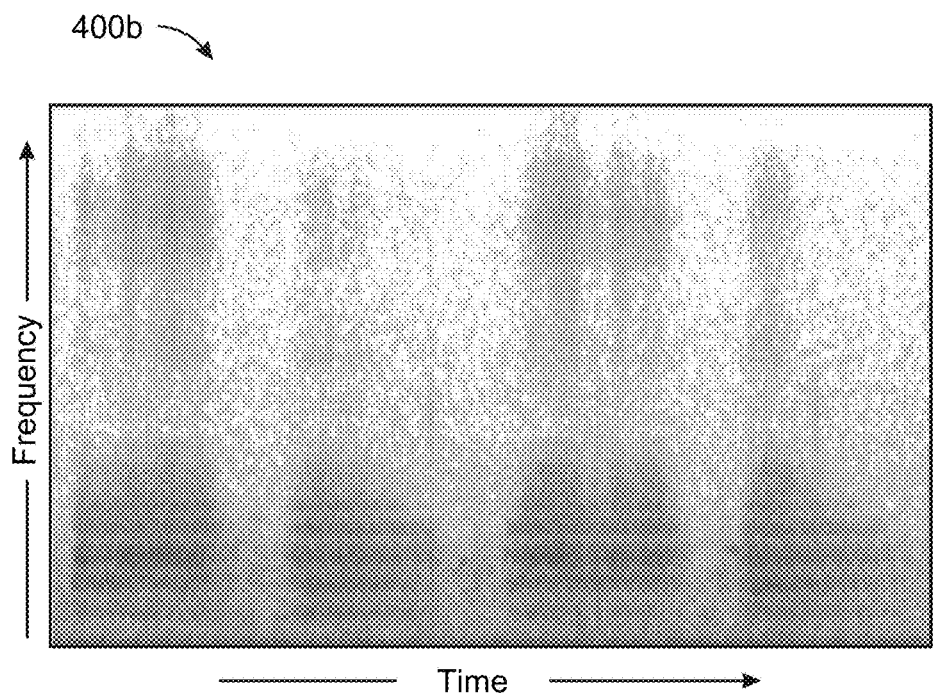
FIGS. 4A and 4B are example spectrograms corresponding to different modes of breathing.
Figure 4A:
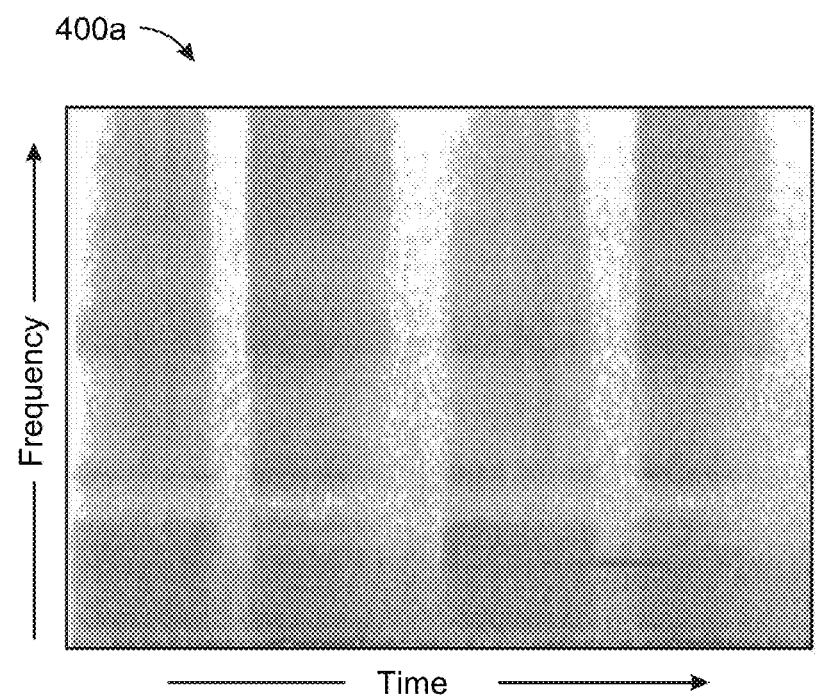

So-called mouth breathing (breathing through one's mouth rather than nose) is another example trigger mode that mode identifier 118 is capable of recognizing. Mouth breathing has been associated with high blood pressure, poor sleep, sleep apnea, snoring, gum disease, halitosis, increased stress, decreased productivity, and even facial deformities. Mouth breathing can be an unconscious action. Mouth breathing is often more rapid than is normal breathing; is more likely to be audible; may be punctuated by sighs; and typically involves movements of an individual's upper chest. Due to the difference in the airway structure as one breathes through the mouth as opposed to the nose, the acoustic characteristics of mouth breathing differ from that of normal breathing. An example difference between the characteristics of mouth breathing and normal breathing is illustrated by the spectrograms shown in FIGS. 4A and 4B, in which spectrogram 400a is generated in response to normal breathing and spectrogram 4b is generated in response to mouth breathing. Energy distribution at different frequencies exhibits differences between a normal mode and mouth-breathing mode. Lower frequency sound exhibits a different resonance pattern in response to mouth breathing as compared to normal breathing.

In certain embodiments, mode identifier 118 detects the user's mouth breathing based on extracted sound features including, for example, one or more of MFCCs, log spectrograms, envelopes, zero crossing rates, spectral roll-offs, and chroma features. Mode identifier 118 can also detect mouth breathing based on linear combinations of the different sound features. Based on one or more of the various sound-based features and/or a linear combination thereof, mode identifier 118 identifies mouth breathing by comparing sound features extracted during monitoring of user's breathing with one or more predetermined thresholds specific to the user. In one embodiment, mode identifier 118 determines power spectral density between 1500 Hz to 2100 Hz, spectral spread, and spectral centroid based on features extracted from signals generated in response to the user's breathing and compares the features against predetermined thresholds.

Figure 5A:
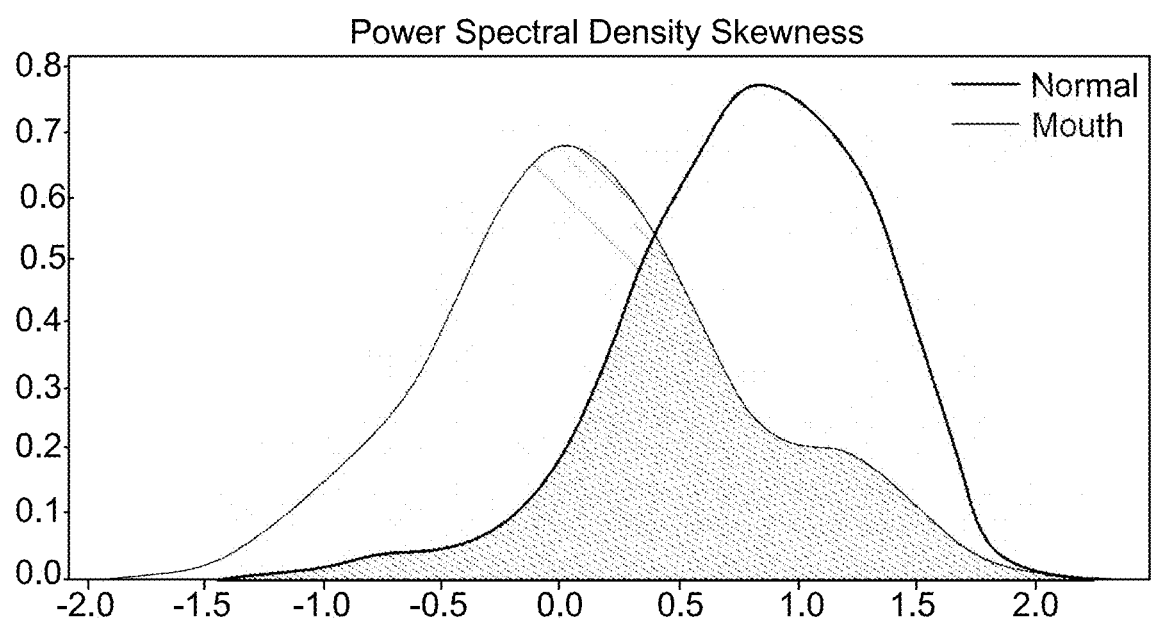
FIGS. 5A, 5B, and 5C are example distribution plots of distinct features of normal modes and mouth breathing nodes.
Figure 5B:
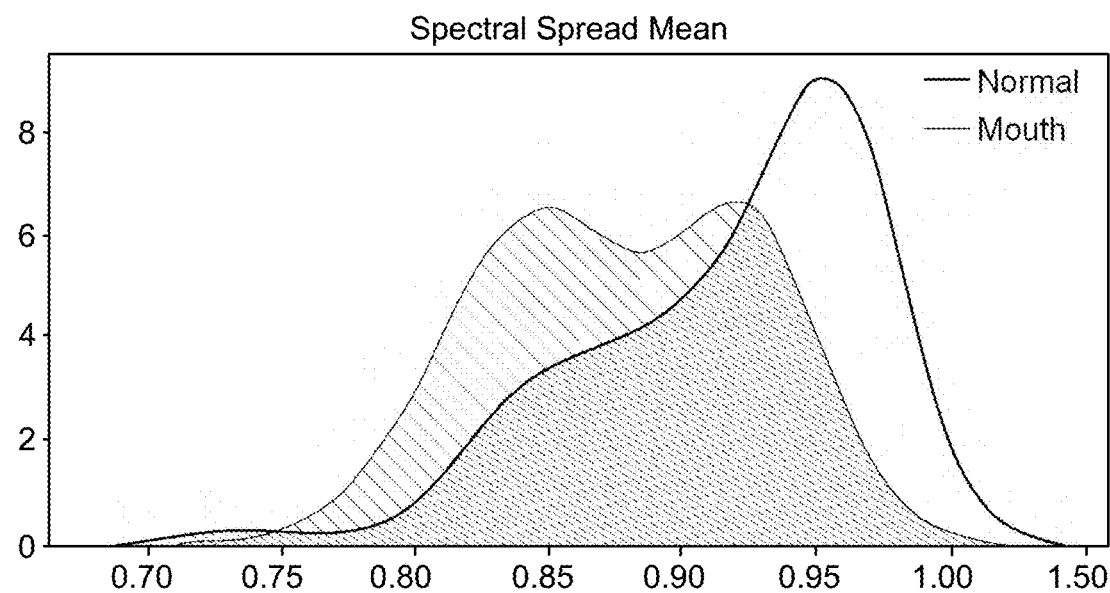
Figure 5C:
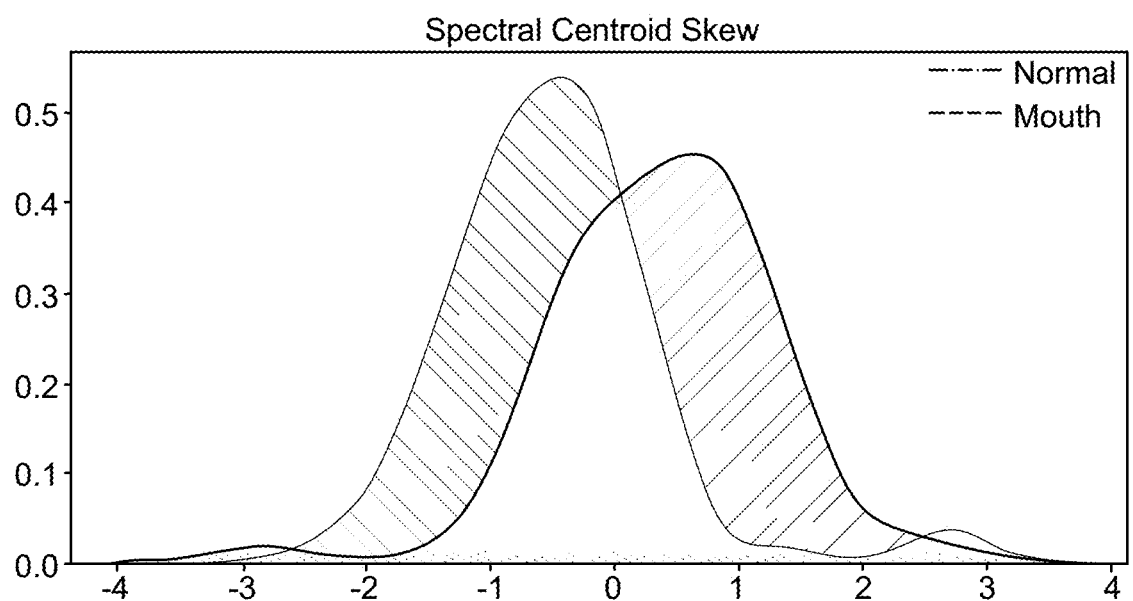

FIGS. 5A, 5B, and 5C are example distribution plots that show the separability of features corresponding to a normal breathing mode and mouth breathing mode. FIG. 5A is a plot showing skewness of power spectral densities (e.g., computing using the Welch periodogram method) with respect to normal and mouth breathing. FIG. 5B is a plot of spreads of spectral mean with respect to normal and mouth breathing. FIG. 5C is a plot showing skewness of spectral centroids with respect to normal and mouth breathing. Thus, leveraging the described separability, mode identifier 118 can detect the user's mouth breathing by comparing the one or more of the various sound-based features and/or a linear combination thereof captured from the user's current breathing with one or more predetermined thresholds corresponding to the extracted features. In other embodiments, mode identifier 118 implements a ML model (e.g., CNN, RNN) specifically trained to identify mouth breathing based on a comparison of the user's current breathing with a learned baseline. In still another embodiment, mode identifier 118 identifies mouth breathing by the user based on signals generated by motion sensor(s) 120 (e.g., earbud IMU) in response to user movements (e.g., torso and head movement). Mode identifier 118 can combine motion data with extracted sound features to detect mouth breathing.

Optional mode responder 122 generates output 124 in response to mode identifier 118 identifying that the current mode of the user's breathing corresponds to a trigger mode (e.g., shallow breathing, mouth breathing). Mode responder 122 is capable of generating output 124 in real-time and conveys output 124 to the user via interface 102. Output 124 is correlated with the specific trigger mode identified by mode identifier 118 and can act as a nudge to the user to engage in mindful breathing to correct the user's current mode of breathing.

Output 124 can comprise a notice, instruction, or other nudge. A notice can indicate to the user the type of trigger mode detected. An instruction can prescribe a type and/or manner of mindful breathing to undertake depending on the nature of the trigger mode identified by mode identifier 118. In some embodiments, mode responder 122 can initially convey a notice and, if the trigger mode is identified anew by mode identifier 118 within a predetermined time, mode responder can follow the notice with an explicit instruction. Output 124 can be conveyed visually via a graphical user interface (GUI) of a display and/or audibly via a speaker of the device in which system 100 is integrated.

Optional contextualizer 126 can determine different contexts of the user's breathing based on different types of data. A context can include a physiological context associated with the user's physical state. The physical state is linked to the user's breathing directly (e.g., breathing rate, breathing symmetry, breathing depth) and/or inferentially (e.g., heart rate, heart rate variability). A context additionally or alternatively can include the user's psychological state (e.g., stressed, anxious, excited) inferred from the user's breathing. Context also can include a social state of the user, such as engaging in a conversation. A context additionally or alternatively can include intrinsic context independent of the user's breathing, such as the user's age, gender, and/or general health. Intrinsic context data specific to the user can be electronically stored, for example, in the memory of the user's device in which system 100 is implemented.

Contextualizer 126 is capable of operating cooperatively with mode identifier 118 to provide a context (e.g., physiological, psychological, and/or social) to the trigger modes identified by mode identifier 118 as the user's breathing is monitored. Knowledge about the context of the user's breathing enhances the ability of mode responder 122 to generate an efficacious breathing nudge (e.g., breathing instruction) in response to a triggering mode and/or event. A contextualized trigger mode or event can invoke a response by mode responder 122, which conveys a nudge to the user prompting the user to engage in mindful breathing (e.g., breathing exercise). For example, system 100 can passively monitor the user's breathing and, if mode identifier 118 detects a trigger mode (e.g., shallow breathing, mouth breathing) that persists a predetermined time (e.g., thirty minutes), then mode responder 122 responds by conveying a nudge to the user. The mode responder 122 is triggered to convey a nudge (e.g., notification breathing instruction) that is correlated with the trigger mode identified by mode identifier 118. Thus, operatively, system 100 can make the user aware of habitual breathing irregularities and/or occasional, unconscious lapses from proper breathing such as shallow breathing or mouth breathing. System 100, moreover, provides output 124 (e.g., notification, breathing instruction) to nudge the user to respond to the irregular or improper breathing by engaging in mindful breathing. Accordingly, depending on the context, output 124 can be explicit instruction to the user to engage in a specific type of mindful breathing in a prescribed manner. The mindful breathing may be particularly adapted to the trigger mode detected by mode detector 118. For example, if the user is mouth breathing, then mindful breathing corresponds to the user closing the mouth and breathing through the nose. If, for example, the user is breathing shallowly, then mindful breathing corresponds to the user breathing more deeply.

Given the capability of contextualizer 124 to contextualize the user's breathing in a social context, mode responder 122 may respond to a trigger mode or event that is appropriate given the user's current social situation. For example, because mindful breathing (e.g., breathing exercises) can be socially distracting, contextualizer 126 can detect social settings based on acoustic signals (e.g., detecting sounds of on-going conversations) and respond accordingly, such as delaying a nudge during a social activity so as to avoid distracting or annoying the user or someone with whom the user is socially engaging at the moment. Contextualizer 126 can detect conversations specifically, for example, based on detecting symmetry patterns (e.g., inhalation-to-exhalation ratio) in the user's breathing. For example, an inhalation-to-exhalation ratio for speech breathing is lower than that for regular breathing (0.5).

The efficacy of nudges conveyed to the user by mode responder 122 can vary depending on factors such as the time of day or day of week that the nudge is conveyed to the user, as well as factors intrinsic to the user such as age, gender, and/or general health of the user. Taking these contexts into account for conveying a nudge to the user heightens the nudge's efficacy and ensures that the nudge conveyed to the user more effectively assists the user in managing and improving the user's breathing habits. As described above, the nudge can be conveyed in real-time visually (e.g., via GUI) and/or audibly (e.g., via speaker) with the device in which system 100 is implemented.

System 100 can implement decision rules for triggering which breathing nudges are conveyed and when based on the different determinations with respect to breathing phase, mode, and/or breathing context. For example, a specific breathing nudge can be triggered in response to mode identifier 118 determining that the user is exhibiting shallow breathing (e.g., breathing depth less than fifty percent) and that user's heart rate has remained elevated (e.g., ten percent over threshold) for a predetermined time (thirty minutes) and that the user is not currently engaged in a conversation. The nudge can instruct the user to engage in a prescribed breathing activity.

Optionally, the decision rules can be based on user preferences input to system 100 by the user via interface 102 of the device in which system 100 is implemented. The user preferences can personalize the triggering of a breathing nudge by mode responder 122. In certain other embodiments, system 100 can use ML to automatically learn the user preferences. Decision rules based on expressed user input or learned through ML can correspond to a fitness goal of the user, for example. In other embodiments, the device in which system 100 is implemented can communicatively couple via a wireless or wired connection with another device, such as one used by a doctor, therapist, or physical trainer who inputs data to system 100 on behalf of the user and when authorized by the user. The data input is used by system 100 to construct decision rules personalized for the user. When the device is worn or carried by the user, system 100 can passively monitor the user's breathing and mode identifier 118 can detect triggering modes or events, and according to the decision rules, mode responder 122 can respond by conveying a nudge prompting the user to perform mindful breathing based on stored preferences of the user.

System 100 can be used in a device to passively monitor the user's breathing on a selective, continuous, or near-continuous basis. To facilitate the monitoring, especially with respect to continuous or near-continuous monitoring, pre-processor 110 can perform additional functions to reduce power consumption, as well as address certain privacy concerns associated with the use of recorded audio. For example, when implemented in earbuds, system 100 can detect whether the earbuds are in use and placed in the user's ears before beginning collection and processing of acoustic data. System 100 can use features such as the L2 norm of a 3-axis motion sensor (e.g., IMU), the standard deviation and/or derivatives signal waveforms, and/or signal entropy as input to a decision tree classifier, which using such the features, can determine whether the earbuds are in use and placed in the user's ears.

During passive monitoring of the user's breathing, system 100 also identifies passive breathing segments that provide reliable inputs to classifier 106 and other processing elements of system 100. For example, when system 100 is implemented in earbuds that system 100 determines are in use and placed in the user's ears, system 100 is capable of continuously tracking the user's breathing based on IMU-detected head motion of the user. System 100 is capable of using motion data captured with the earbud IMUs to distinguish non-breathing head motions (any motion other than that induced by the user's breathing) from those stemming from the user's breathing. In selectively performing breathing detection and feature extraction, system 100 only undertakes detection and extraction actions if the detected motion indicates that reliable breathing segments are obtainable. Because the accuracy of an IMU-based passive detection algorithm is affected by vigorous head motion, system 100 partitions the sensor data stream into segments lying between intervals corresponding to vigorous head motions. System 100 determines whether a segment is reliable for performing breathing analysis with the other elements of system 100 based on the segment's duration. The greater the duration of the segment, above a predetermined minimum (e.g., twenty seconds), the more likely the data collected is reliable. Accordingly, system 100 uses the duration of the segment as a quality indicator and selects only segments meeting the criteria for reliable passive data segments for determining breathing modes and triggering breathing nudges for conveyance to the user.

Figure 6A:
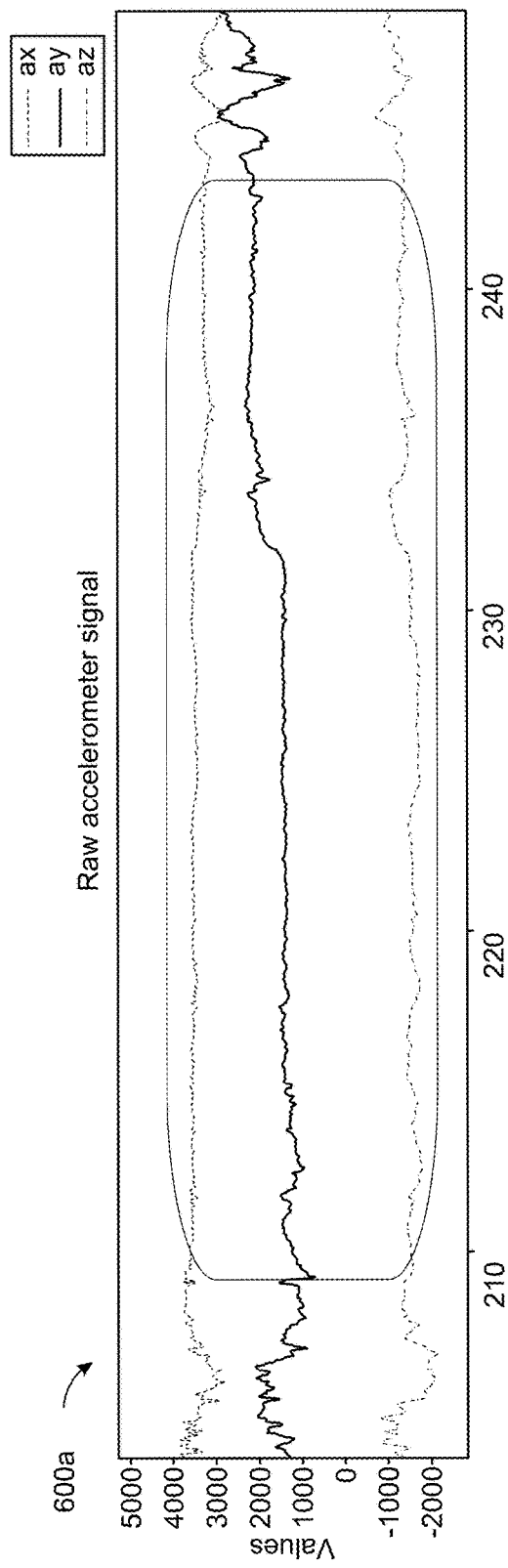
FIGS. 6A and 6B are, respectively, an example raw sensor signal waveform and corresponding three-dimensional quaternions.
Figure 6B:
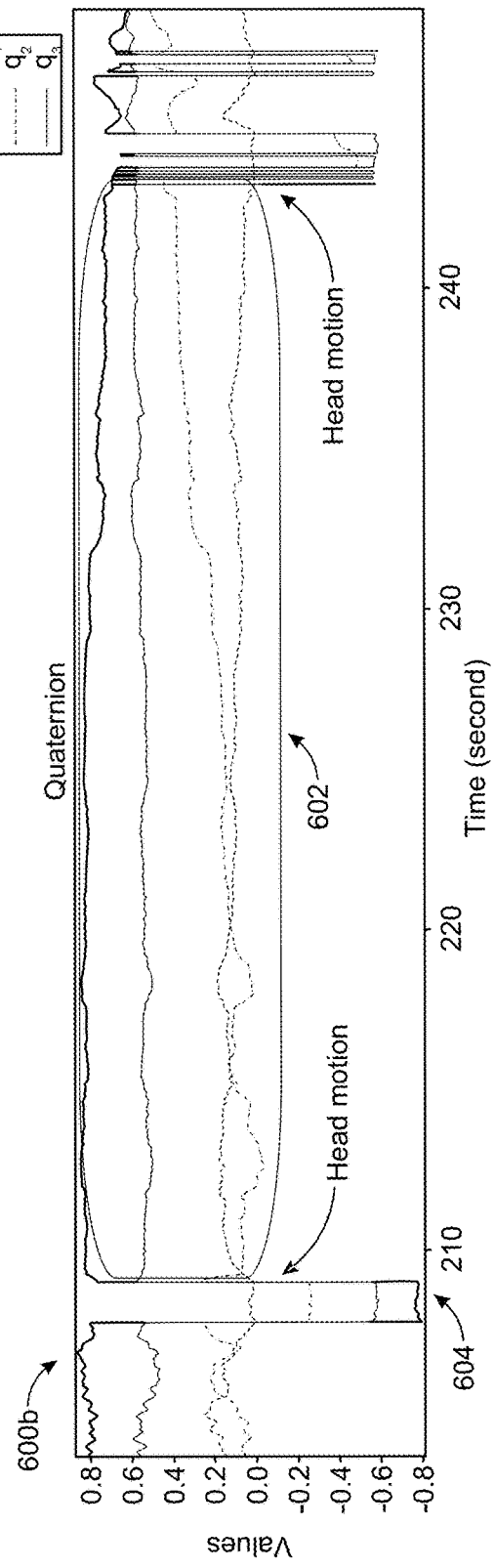

FIGS. 6A and 6B illustrate that three-dimensional quaternion head motion tracking can identify transition points at the respective boundaries of a passive breathing segment. Graph 600a of FIG. 6A plots the raw signal generated by a motion sensor (e.g., IMU) in response to a subject's head motion over a predetermined interval. Graph 600b of FIG. 6B plots the corresponding three-dimensional quaternion with respect to the same head motion over the same interval, with segment 602 corresponding to a passive breathing segment bounded by portions 604 and 606 corresponding to sharp head movements.

Figure 7A:
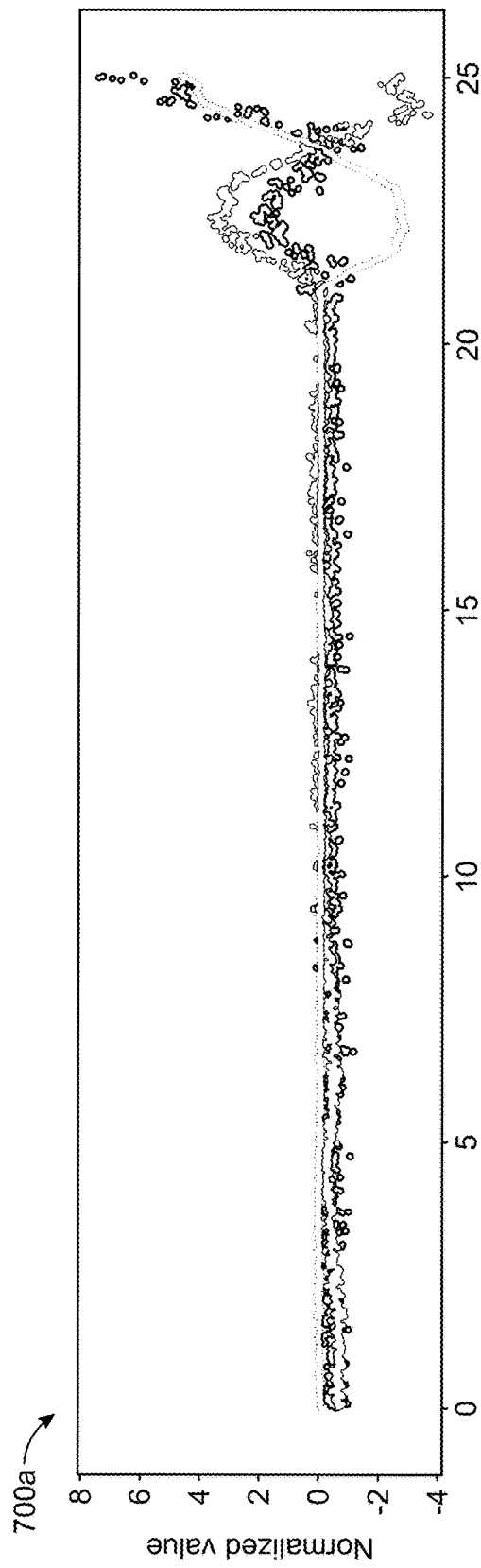
FIGS. 7A and 7B are, respectively, an example normalized sensor signal waveform and corresponding standard deviations.
Figure 7B:
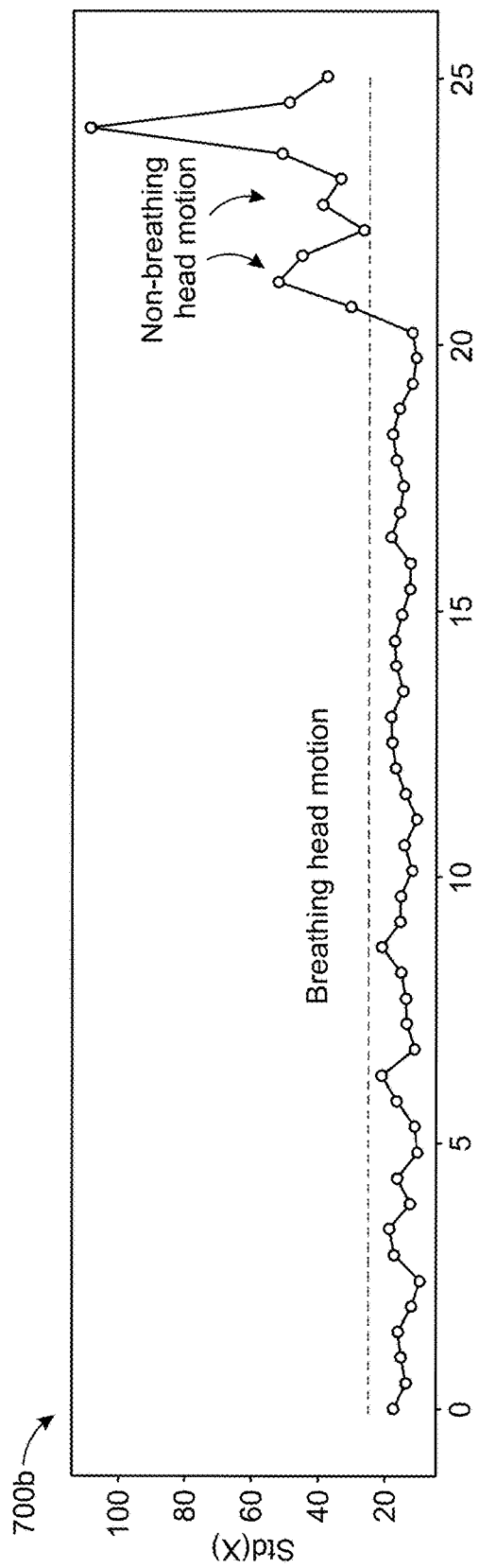

System 100, in another embodiment, uses data obtained from an axis of an inertial sensor to detect the passive breathing segment. The standard deviation of a head motion signal generated over a predetermined interval by a single axis of motion sensor (e.g., earbud IMU) can identify breathing head motion. FIGS. 7A and 7B illustrate the use of a standard deviation. Graph 700a of FIG. 7A plots a 500 ms segment of a raw signal generated by the single axis, and graph 700b of FIG. 7B plots the corresponding standard deviation. Note that for breathing head motion the preponderance of the standard deviations of the signal lie below threshold 702. System 100 can use a threshold determined from a statistical analysis of signals generated using a set of subjects (e.g., thirty) to identify breathing head motion and non-breathing head motion. The non-breathing head motion can occur at the beginning, middle or end of the signal window. Based on the position of the non-breathing head motion detected (standard deviation less than threshold), a detection algorithm detects data islands corresponding to non-breathing head motion and breathing head motion. In accordance with this embodiment, system 100 discards the data island corresponding to non-breathing head motion and uses the retained data as input to the other elements of system 100 for performing breathing analyses.

In certain embodiments, system 100 provides biofeedback to the user in response to tracking the user's breathing. System 100 can track the user's breathing using audio-based tracking, motion-based tracking, or a combination of audio-based and motion-based tracking. With audio-based tracking, system 100 tracks real-time breathing phases that are determined from audio segments having a predetermined duration (e.g., 200 ms). Operatively, during the tracking, system 100 filters acoustic signals to remove high frequency noise and converts the filtered signals into a time-versus-energy two-dimensional spectrogram. System 100 sums energy levels distributed across the frequency bands and converts the two-dimensional spectrogram into one-dimensional timeseries data. In one embodiment, system 100 applies a bandpass filter between 0.25 Hz and 2.5 Hz to remove undesirable frequencies from the one-dimensional timeseries data. Based on the amplitude of the one-dimensional timeseries data, system 100 admits or rejects the current audio segment. If the amplitude of the current audio segment is above a predetermined threshold, system 100 extracts acoustic features from the one-dimensional time-series data (e.g., MFCC, chroma, spectral spread, relative spectral density) and, based on the extracted acoustic features, classifies the current segment as either a portion of an on-going inhalation or portion of an exhalation segment.

In some embodiments, system 100 takes the last 30 seconds of the breathing segment to reduce false detection in seeking to identify a phase switching from inhale to exhale or exhale to inhale. Once the phase switching point is detected, system 100 conveys the information in real-time to a visual or auditory feedback engine operatively coupled with system 100 to the user in real-time via a GUI or other user interface. The user can compare the target pattern and the actual breathing pattern and adjust the user's breathing based on the real-time feedback to achieve the best performance.

With audio-based tracking, system 100 tracks real-time breathing phases based on sensor-generated motion data captured by motion sensor(s) 120. In certain embodiments, system 100 is integrated in a pair of earbuds worn by the user, and the motion data is generated by an earbud IMU from 200 ms data segments. The IMU-generated motion data can be obtained from a 3-axis accelerometer, 3-axis gyroscope, 3-axis magnetometer, and/or a combination thereof. System 100 can perform signal smoothing with a series of filters applied to the motion data from each axis to remove high-frequency noises. System 100 normalizes IMU-generated signals using, in certain embodiments, a bandpass filter (e.g., [0.13 Hz, 0.66 Hz]) and subtracts the signal mean to reduce the signal drift. System 100 sums signals generated by the three axes and normalizes and smooths the resultant sum. The described method of processing IMU signals may be performed independently of the orientation of the device (e.g., earbud) in which the IMU is embedded. Lastly, system 100 computes the derivative of the resultant signal, detecting phase switching points (inhale-to-exhale and exhale-to-inhale) in real-time by detecting the sign change of the signal derivative. In other embodiments, system 100 can reduce the likelihood of an erroneous or false phase switching determination from a noisy signal by determining both the sign change and the amplitude change. In some embodiments, system 100 can determine a breathing mode (e.g., shallow breathing) in tracking the user's breathing based on both sound energy and breathing depth, as described above.

In still another embodiment, system 100 generates real-time biofeedback by fusing both motion (e.g., IMU-generated) and acoustic data from sensor(s) (e.g., earbud IMU) to accurately detect the breathing phase and the rate of airflow of the user's breathing. System 100 generates one increasing trend for inhalation phase and one decreasing trend for the exhalation phase. The spectrogram, derived from a one-dimensional signal from the acoustic data, will generate one sound energy cycle for the inhalation phase and one sound energy cycle for the exhalation phase. By combining the direction from the IMU data and breathing phase sound energy elevation, system 100 can determine the breathing phases in real-time and provide biofeedback to the user.

In yet another embodiment, system 100 is implemented in a device that communicatively couples with another device and combines data generated by both the coupled device and the device in which system 100 is integrated. By processing the combined data gained by the coupling of two devices, system 100 can provide greater predictive accuracy. For example, the breathing guidance can be a companion app on a device (e.g., smartphone, smartwatch). Therefore, a device microphone can also capture the breathing sounds of the user. If there is confusion between the breathing trend detected with a motion sensor (e.g., earbud IMU) and that detected with acoustic sensor (e.g., microphone) of a device (e.g., earbud), the audio from the second device (e.g., smartphone) may be used to resolve the conflict. Resolution may be based on majority voting or based on the signal to noise ratio (SNR), where the signal whose SNR is higher is given priority over the signal whose SNR is lower. In another embodiment, system 100 can combine motion sensor-based data from one device (e.g., earbud) with acoustic sensor-based audio from the other device (e.g., smartphone) to track breathing phase in real-time and provide biofeedback.

System 100, in other embodiments, monitors a user's exercise efficiency. Exercise efficiency can comprise two elements. First, an assessed similarity between actual and target breathing patterns, and second, a system-determined impact of prescribed mindful breathing on the user for relaxing from the physiological exertion experienced during exercise based on analysis of IMU, audio, or a combination thereof to quantify the efficacy of the breathing exercises. If system 100 is implemented in a pair of earbuds, for example, an earbud IMU can generate signals from which can be extracted features for creating data to determine breathing rate, breathing symmetry (e.g., inhalation-to-exhalation ratio), and/or breathing depth for estimating the efficacy of the user performance based on a comparison with the target breathing pattern. The user can set a target breathing pattern (e.g., breathing rate of five breaths per minute or six-second inhalation and six-second exhalation) with input into the device in which system 100 is implemented. System 100 automatically analyzes IMU-based data and audio data to extract the actual breathing pattern, based on which system 100 determines a similarity between the target pattern and the actual pattern to compute the efficacy of the user performance. The user's breathing patterns can be a sequence of the duration of the user's inhalation and exhalation breathing phases. The breathing pattern can correspond to the user's breathing rate in breaths per minute. User performance can provide a basis for the biofeedback provided to the user.

According to another embodiment, system 100 can assess the impact of the breathing exercises on the user. System 100 can be implemented, for example, in a pair of earbuds, and data upsampling can be performed by combining the left and right earbuds IMU data in ascending order based on the timestamps of the data. Upsampling the IMU sensor data can enable the earbuds to extract the user's heart rate by capturing head motion due to the motion caused by the user's heartbeat. Thus system 100 can passively determine a user's level of physiological excitation using a predetermined heart rate elevation threshold and quantify the impact of the breathing exercises by comparing the heart rate before, during, and after the exercises are performed by the user. The comparison can be the heart rate differences between before and after the exercises. System 100 can maintain a mapping between the exercise type and user's breathing pattern with the reduction in the user's heart rate. The same exercise pattern will have a different impact on different users. Based on the mapping, system 100 can recommend more effective, personalized breathing exercises based on the system-determined physiological excitation level.

System 100, in another embodiment, can also track the context (e.g., time, location, social setting) simultaneously with tracking the user's breathing, and based on both, can recommend breathing exercises determined to be better suited for the user in a current context. In another embodiment, system 100 can track the heart rate trajectories during the exercise and can match the user's breathing pattern during exercise with the heart rate trajectories to determine the efficacy of the breathing exercises, which can be used to recommend mindful breathing to calm the user down after exercise-induced physiological excitation. In yet another embodiment, system 100 can extract heart rate variability measurements such as RMSSD, PNN50, and LF/HF from sensor-generated data created with a device (e.g., earbuds) to assess user stress and breathing exercise performance efficacy. Improvement in the user's breathing can be defined by the rate of heart rate recovery, according to which the user's heart rate comes back to the baseline after the exercise. If one particular breathing exercise helps the user more quickly recover from the stressful situation than another exercises, then that particular exercise is determined to be more effective than the others.

Figure 8:
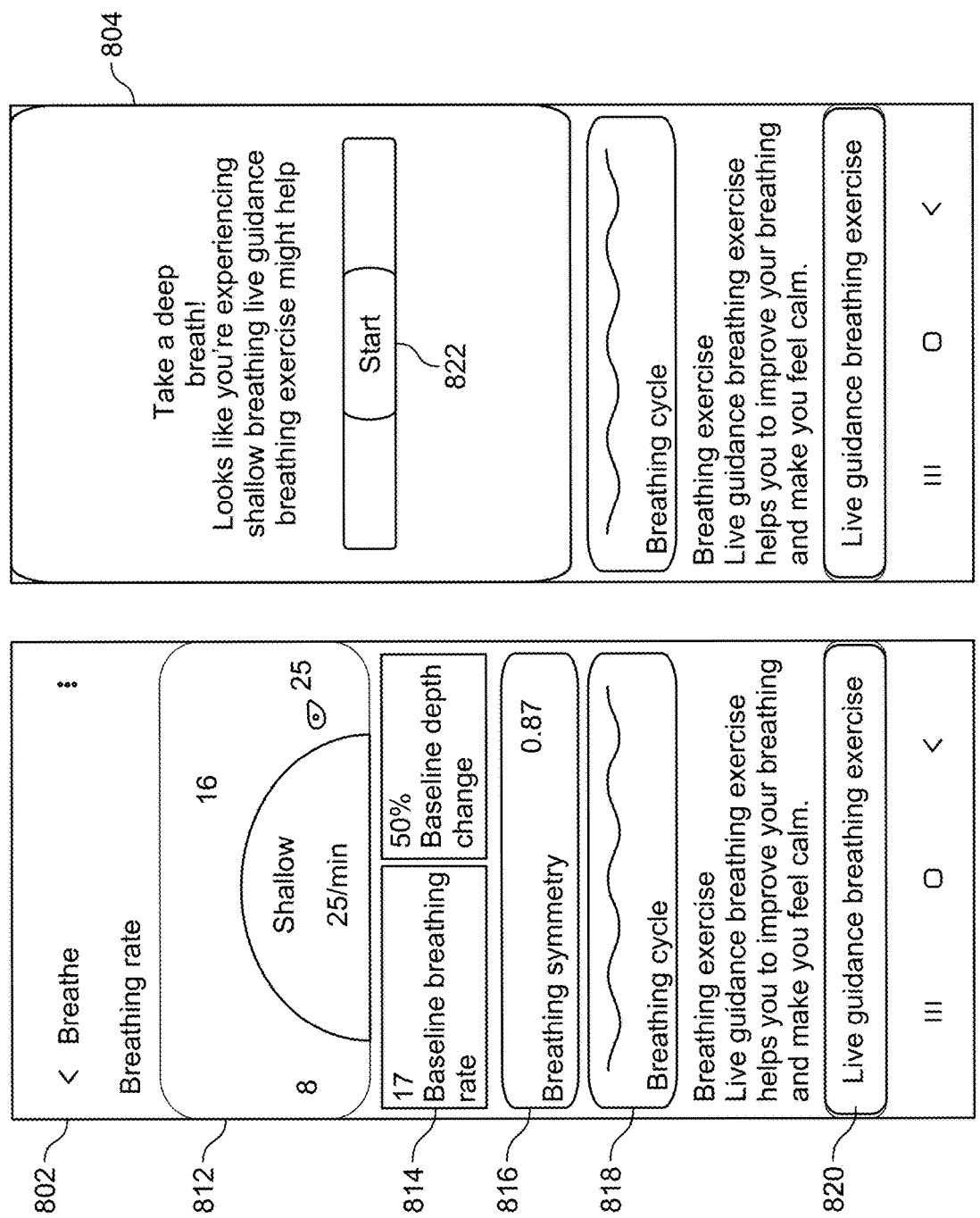
FIG. 8 illustrates example graphical user interfaces.
Figure 8:
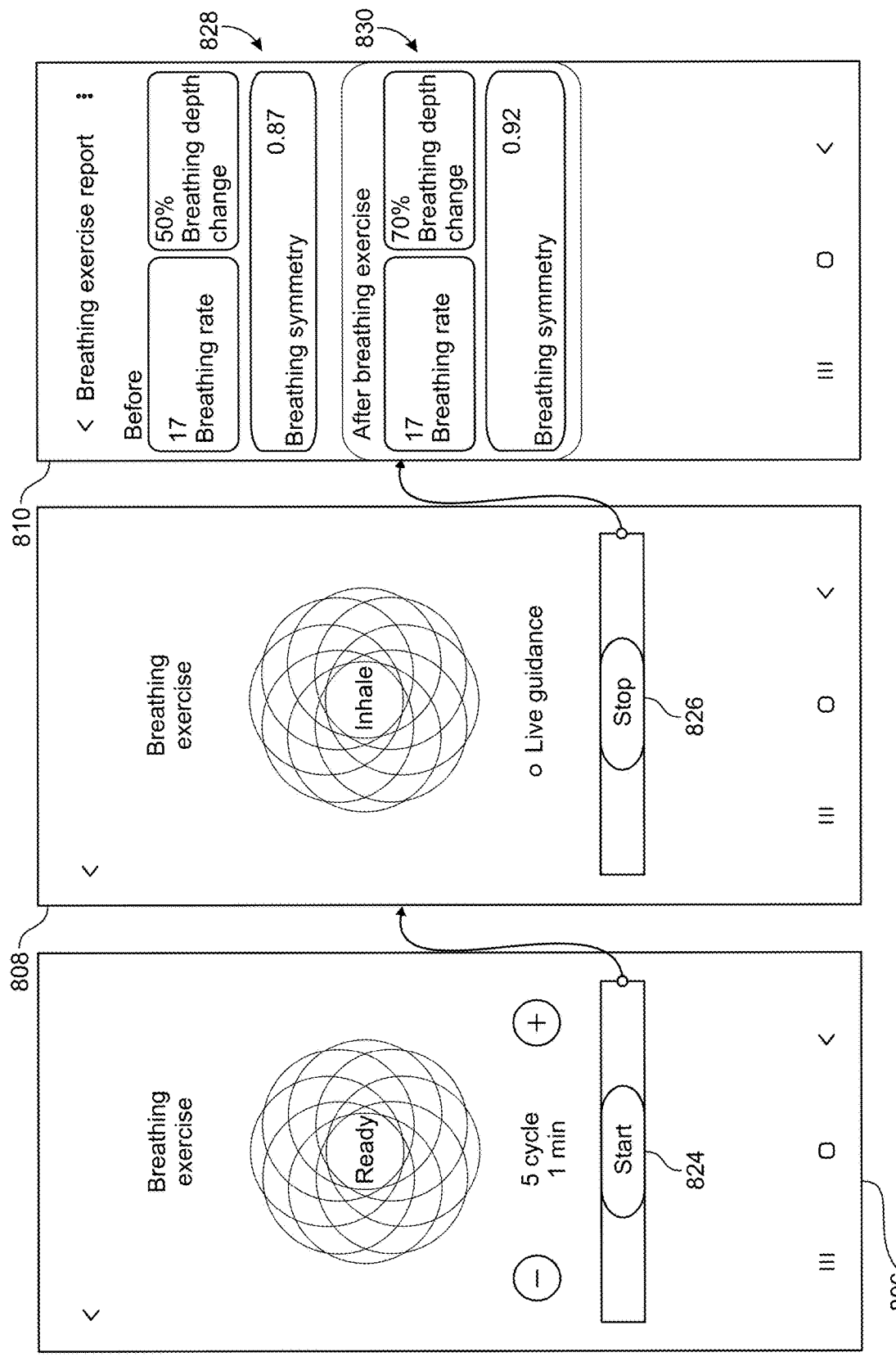

FIG. 8 illustrates a series of GUIs 802, 804, 806, 808, and 810 generated by system 100, for example, on a touchscreen display of the device in which system 100 is implemented. GUIs 802-810 are progressively presented to the user on the touchscreen display to assist in managing the user's breathing. Initially, using acoustic and/or motion data as described above, system 100 determines characteristics of the user's current mode of breathing. GUI 802 presents windows 812, 814, 816, 818, and 820 indicating the characteristics. Window 812 displays the user's current breathing rate. Windows 814 display on one side the user's already-determined (as described above) baseline breathing rate and on the other side a change in breathing depth. Window 816 displays the user's current breathing symmetry (e.g., ratio of breathing phases), and window 818 displays the cyclical pattern of the user's breathing. Window 820 provides a touch-responsive prompt that the user can touch to initiate a "live guidance breathing exercises" program implemented with system 100.

GUI 804 provides a visually displayed nudge to the user. The nudge both notifies the user that user's current breathing mode corresponds to a shallow breathing trigger mode, and instructs the user to take a deep breath. Touch-responsive prompt 822 allows the user to start system 100's "live guidance breathing exercises" program with an appropriate breathing exercise. GUI 806 allows the user to set a target breathing pattern (e.g., breathing rate of 5 bpm) and initiate with touch-responsive prompt 824 the monitoring of the user's breathing while engaging in the breathing exercise. GUI 808 enables the user to stop breathing monitoring using touch-responsive prompt 826. System 100 in response to the user's cessation of the breathing exercises generates a breathing exercise report, which is displayed by GUI 810. Window 828 of GUI 810 displays a summary of the user's pre-exercise breathing characteristics, and window 830 displays a summary of the user's breathing characteristics at the conclusion of the breathing exercise. System 100 can determine from a comparison of the pre- and post-exercises breathing characteristics the quality of the user's exercise performance and the efficacy of the exercises in improving the user's breathing.

Figure 9:
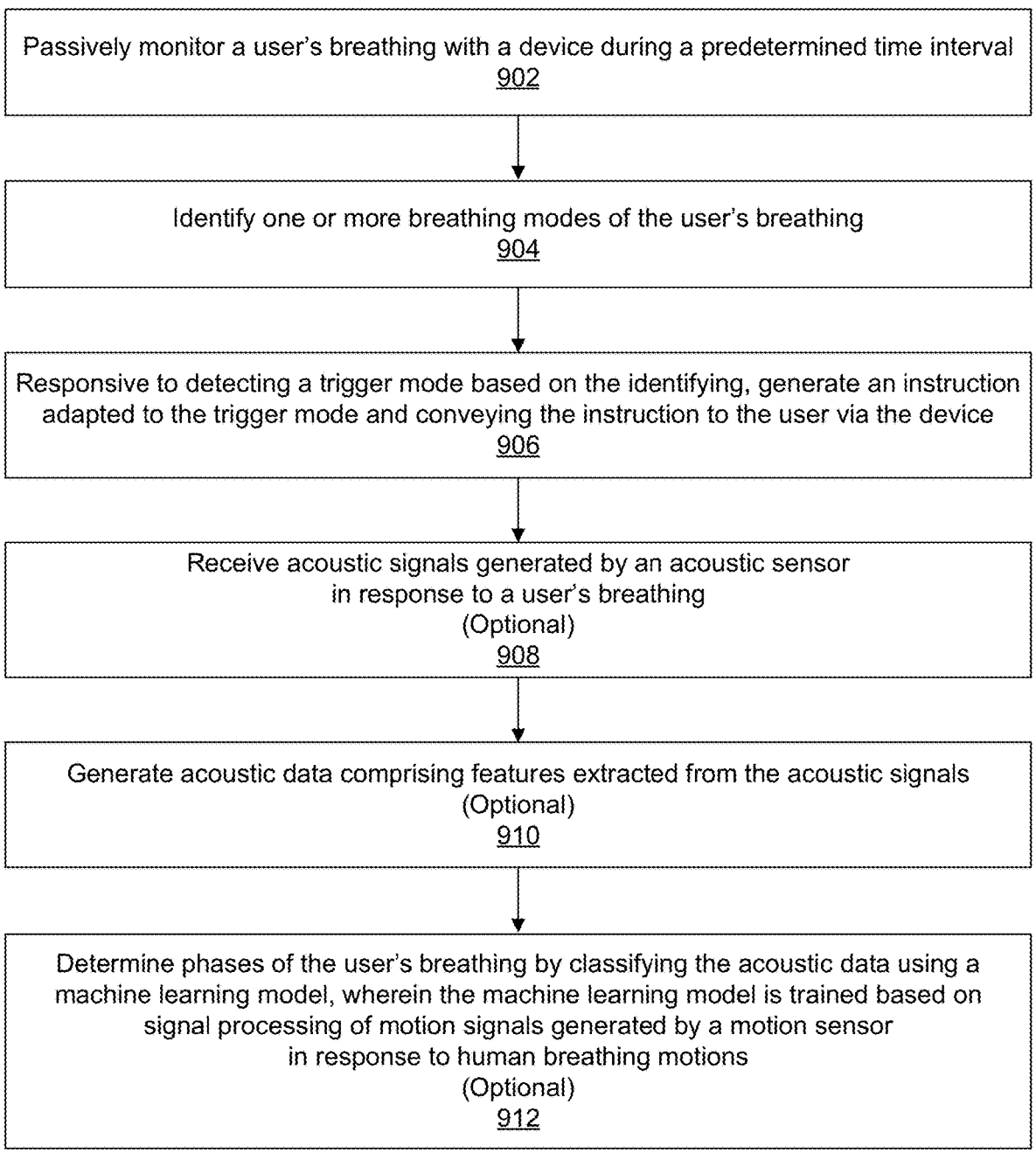
FIG. 9 is a flowchart of an example method of monitoring a user's breathing with a device.

FIG. 9 is a flowchart of example method 900 of monitoring a user's breathing. Method 900 can be performed by a system the same or similar to the systems described with respect to FIGS. 1-7.

At block 902, the system passively monitors the user's breathing with a device during a predetermined time interval. The system at block 904, identifies one or more breathing modes of the user's breathing. At block 906, in response to detecting a trigger mode based on the identifying, the system generates an instruction adapted to the trigger mode and conveys the instruction to the user via the device. The trigger mode can correspond to shallow breathing or mouth breathing by the user. The instruction can be conveyed to the user visually (e.g., via GUI) and/or audibly (e.g., via speaker) with the device in which the system is implemented. The instruction can be conveyed to the user in real-time.

At block 908, the system optionally receives acoustic signals generated by an acoustic sensor in response to a user's breathing. The system at block 910 optionally can generate acoustic data comprising features extracted from the acoustic signals. At block 912, the system optionally can determine the phases of the user's breathing by classifying the acoustic data using a machine learning model. The machine learning model can be trained based on signal processing of motion signals generated by a motion sensor in response to human breathing motions. Although trained using signal processing of motion signals, once trained, the ML model is trained to classify acoustic data. The determination of the phases of user's breathing can be performed in real-time using a device that monitors the user's breathing during a predetermined time interval.

The ML model, in certain embodiments, is a deep learning neural network. The deep learning neural network can be a CNN model, the input to which comprises normalized 40×22 feature matrices whose elements are MFCC values extracted from the acoustic signals. In other embodiments, extracted features can additionally or alternatively include log spectrograms and/or other breathing-related features.

Based on distinct acoustic features of different phases of breathing, the ML model classifies acoustic data as more likely associated with one phase than another. For example, inhalation duration is typically briefer than is exhalation duration. The frequency distributions of inhalation and exhalation phases likewise vary, for example. Exhalation phases tend to have a higher mean amplitude than inhalation phases. The average energies of inhalation and exhalation phases, respectively, are 19.08 dB and 69.76 dB. The SNR of inhalation and exhalation phases are −44.98 dB and −36.12 dB, respectively. The SNR and energy measurements also reflect lower amplitude in the inhalation phase. The different values of the extracted features reflect the different phases of the user's breathing. The ML model is trained to classify the acoustic data according to values of the extracted features, based on which the system determines the phases of the user's breathing in real-time.

The ML model can be trained by obtaining acoustic training data created from a series of sensor-generated acoustic signals generated in response to the breathing of one or more human subjects. The training data can be obtained by monitoring the breathing of the user, alone or in addition to breathing of one or more other individuals. The training data can be obtained from monitoring the breathing of multiple subjects of the user. The subjects can include healthy individuals. The subjects also can include individuals selected from one or more populations, each population afflicted with a different respiratory condition (e.g., asthma, COPD, viral infection), thereby enabling the ML model to differentiate among different health-related breathing conditions in classifying the breathing phases of the user.

The acoustic training data can be annotated, the annotation based on the sensor-generated motion signals. The training data provides examples with which the ML model can learn to classify acoustic data. Annotating assigns each example a label that identifies the correct classification. The sensor-generated motion signals thus identify the correct classification for labeling the examples. The sensor-generated motion signals are generated in response to the breathing of the one or more subjects and are generated simultaneously with generating the sensor-generated acoustic signals generated in response to the breathing of the one or more subjects.

In response to detecting a trigger mode in the user's breathing, the system also can identify a breathing context associated with the user. The breathing context can include a physiological context of the user, a psychological context of the user, and/or a social context corresponding to the use. For example, the physiological context may be an elevated heart rate or blood pressure identified by the system, which also detects the user breathing rapidly through the mouth (mouth breathing) and determines extended phases of inhalation in the user's breathing. To prevent the user gulping air, the system, based on the context, can select a nudge to convey to the user, the nudge advising the user to engage in slowed rate of mindful breathing. Similarly, a psychological context such as stress, anger, or overexcitement may cause the user to rapidly take shallow breaths. Based on the context, the system can select a nudge that instructs the user to breathe more slowly and take deeper breaths. In a situation in which no immediate action by the user is necessary, the system may time the conveyance of a nudge based on context. For example, a social context may be a conversation, which the system detects from the sound of human voices. In response to the social context, the system may delay a nudge urging the user to engage in mindful breathing (e.g., deep breathing exercise) that would be distracting or annoying to participants to the conversation.

Implementing method 900, the system can capture with the device the series of sensor-generated acoustic signals during the predetermined time interval. The system can discard one or more of the series of sensor-generated acoustic signals in response to identifying each as an unreliable signal. The system can identify unreliable acoustic signals based on a comparison of multiple phases of the user's breathing. For example, if an acoustic signal is identified as an exhalation (inhalation) but immediately follows or precedes another identified exhalation (inhalation), there is a likelihood that the identification is spurious and that the acoustic signal is unreliable.

Implementing method 900, the system also can convey an instruction to the user via the device. The instruction can instruct the user to perform a mindful breathing exercise in response to identifying a trigger mode of the user's breathing, the identifying based on determining phases of the user's breathing. The system can provide auditory or visual biofeedback to the user via the device based on determining phases of the user's breathing as the user performs the mindful breathing exercise. The biofeedback can be provided in real-time visually (e.g., via GUI) and/or audibly (e.g., via speaker) with the device in which the system is implemented.

The system, in implementing method 900, also can identify a breathing pattern of the user based on determining phases of the user's breathing and can compare the breathing pattern identified with a target pattern specified in response to user input to the device. The system can generate an instruction based on the comparison and can convey the instruction to the user with the device. The system can convey the instruction to the user, for example, visually (e.g., via GUI) and/or audibly (e.g., via speaker) with the device in which the system is implemented. The system can identify a breathing pattern of the user based on determining phases of the user's breathing and a corresponding physiological condition of the user. The breathing pattern can be the user's breathing rate in breaths per minute. The breathing pattern can correspond to the duration of the breathing phases with or without breath-holding between the phases by the user. The breathing pattern also can include breathing depth relative to their baseline (for example, breathing depth should be at least 50 percent higher than their baseline depth).

The system can generate an instruction, based on the breathing pattern and corresponding physiological condition, and can convey the instruction to the user with the device. Again, the system can convey the instruction to the user visually (e.g., via GUI) and/or audibly (e.g., via speaker) with the device in which the system is implemented.

Figure 10:
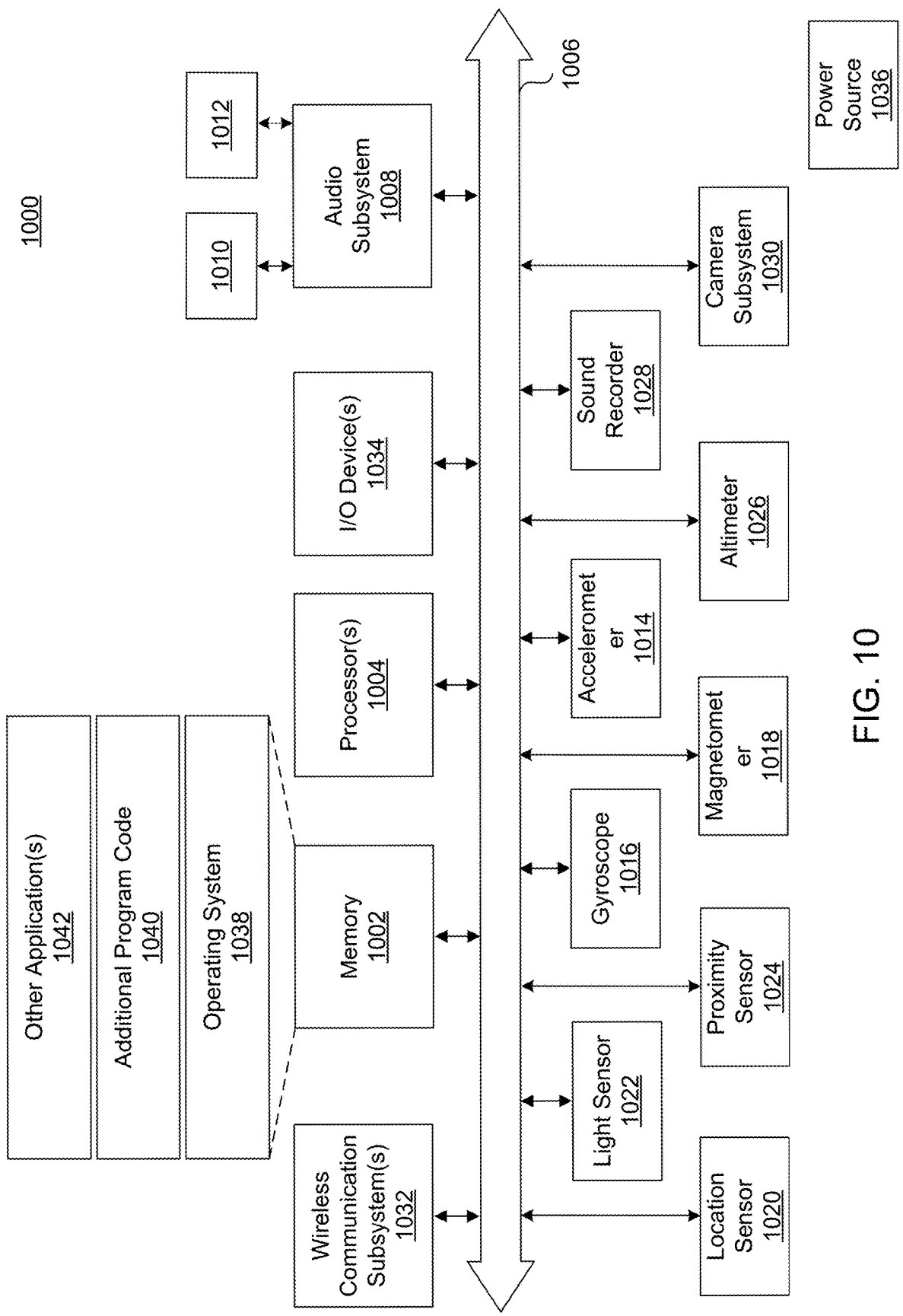
FIG. 10 illustrates an example device in which the system of FIG. 1 can be implemented.

FIG. 10 illustrates example device 1000 in which system 100 can be implemented in accordance with one or more embodiments described within this disclosure. Device 1000 can be a portable device that can be worn by the user (e.g., earbuds, smartwatch, smart glasses) or carried comfortably and conveniently (e.g., smartphone). Device 1000 can include memory 1002, one or more processors 1004 (e.g., image processors, digital signal processors, data processors), and interface circuitry 1006.

In one aspect, memory 1002, processor(s) 1004, and/or interface circuitry 1006 are implemented as separate components. In another aspect, memory 1002, processor(s) 1004, and/or interface circuitry 1006 are integrated in one or more integrated circuits. The various components of device 1000 can be coupled, for example, by one or more communication buses or signal lines (e.g., interconnects and/or wires). In one aspect, memory 1002 may be coupled to interface circuitry 1006 via a memory interface (not shown).

Subsystems, sensors, devices, and/or input/output (I/O) devices can be coupled to interface circuitry 1006 to facilitate the functions and/or operations described herein, including the generation of sensor data. The various sensors, devices, subsystems, and/or I/O devices may be coupled to interface circuitry 1006 directly or through one or more intervening I/O controllers (not shown).

Device 1000 illustratively includes audio subsystem 1008. Audio subsystem 1008 can be operatively coupled to speaker 1010 and microphone 1012 to facilitate voice-enabled functions, such as voice recognition, voice replication, digital recording, audio processing, and telephony functions. Audio subsystem 1000 is able to generate acoustic sensor data. In one or more embodiments, microphone 1012 is utilized as an acoustic sensor. As an acoustic sensor, microphone 1012 can capture acoustic signals generated in response to the user's breathing.

Sensors embedded in device 1000 include accelerometer 1014, gyroscope 1016, and magnetometer 1018. Accelerometer 1014 can be connected to interface circuitry 1006 to provide sensor data that can be used to determine change of speed and direction of movement of a device in three dimensions. Gyroscope 1016 can be connected to interface circuitry 1006 to provide sensor data that can be used to determine orientation and angular velocity. Magnetometer 1018 can be connected to interface circuitry 1006 to provide sensor data that can be used to determine the direction of magnetic North for purposes of directional navigation. In some embodiments, accelerometer 1014, gyroscope 1016, and magnetometer 1018 are integrated as an IMU (e.g., embedded in an earbud and/or other portable device).

Other sensors embedded in device 1000 can include location sensor 1020, light sensor 1022, and proximity sensor 1024 operatively coupled to interface circuitry 1006 to facilitate orientation, lighting, and proximity functions, respectively, of device 1000. Altimeter 1026 can be connected to interface circuitry 1006 to provide sensor data that can be used to determine altitude. Sound recorder 1024 can be connected to interface circuitry 1006 to store recorded sounds.

Camera subsystem 1030 can be coupled to an optical sensor (not shown) that is implemented using any of a variety of technologies. Examples include a charged coupled device (CCD), a complementary metal-oxide semiconductor (CMOS) optical sensor, and the like. Camera subsystem 1030 and optical sensor can be used to facilitate camera functions, such as recording images and/or video clips. In one aspect, image data is a subset of sensor data.

Communication functions can be facilitated through one or more wireless communication subsystems 1032 connected to interface circuitry 1006. Wireless communications subsystem(s) 1033 can include radio frequency receivers and transmitters, optical (e.g., infrared) receivers and transmitters, and so forth. The specific design and implementation of wireless communication subsystem(s) 1032 can depend on the specific type of device 1000 implemented and/or the communication network(s) over which device 1000 is intended to operate.

For purposes of illustration, wireless communication subsystem(s) 1032 can be designed to operate over one or more mobile networks (e.g., GSM, GPRS, EDGE), a Wi-Fi network that may include a WiMax network, a short-range wireless network (e.g., a Bluetooth network), and/or any combination of the foregoing. Wireless communication subsystem(s) 1032 can implement hosting protocols such that device 1000 can be configured as a base station for other wireless devices.

I/O devices 1034 can be coupled to interface circuitry 1006. Examples of I/O devices 1034 include, for example, display devices, touch-sensitive display devices, track pads, keyboards, pointing devices, communication ports (e.g., USB ports), network adapters, buttons, or other physical controls, and so forth. A touch-sensitive device such as a display screen and/or a pad is configured to detect contact, movement, breaks in contact, and the like using any of a variety of touch sensitivity technologies. Example touch-sensitive technologies include capacitive, resistive, infrared, and surface acoustic wave technologies, other proximity sensor arrays or other elements for determining one or more points of contact with a touch-sensitive device, and the like. One or more of I/O devices 1034 can be adapted to control functions of sensors, subsystems, and such of device 1000.

Device 1000 further includes a power source 1036. Power source 1036 is able to provide electrical power to various elements of device 1000. In one embodiment, power source 1036 is implemented as one or more batteries. The batteries may be implemented using any of a variety of different battery technologies, whether disposable (e.g., replaceable) or rechargeable. In another embodiment, power source 1036 is configured to obtain electrical power from an external source and provide power (e.g., DC power) to the elements of device 1000. In the case of a rechargeable battery, power source 1036 further may include circuitry that is able to charge the battery or batteries when coupled to an external power source.

Memory 1002 can include random access memory (e.g., volatile memory) and/or non-volatile memory, such as one or more magnetic disk storage devices, one or more optical storage devices, flash memory, and so forth. Memory 1002 can store operating system 1038, such as LINUX, UNIX, a mobile operating system, an embedded operating system, and the like. Operating system 1038 may include instructions for handling system services and for performing hardware-dependent tasks.

Memory 1002 may store additional program code 1040. Examples of other program code 1040 may include instructions to facilitate communicating with one or more additional devices, one or more computers, and/or one or more servers; graphic user interface processing; processing instructions to facilitate sensor-related functions; phone-related functions; electronic messaging-related functions; Web browsing-related functions; media processing-related functions; GPS and navigation-related functions; security functions; camera-related functions, including Web camera and/or Web video functions; and so forth. Memory 1002 can store instructions and/or program code for implemented a system for determining a user's breathing faces and additional functions the same or similar to those described with respect to example system 100. Memory 1002 can also store one or more other applications 1042.

The various types of instructions and/or program code described are provided for purposes of illustration and not limitation. The program code may be implemented as separate software programs, procedures, or modules. Memory 1002 can include additional instructions or fewer instructions. Moreover, various functions of device 1000 may be implemented in hardware and/or software, including in one or more signal processing and/or application-specific integrated circuits.

Program code stored within memory 1002 and any data used, generated, and/or operated on by device 1000 are functional data structures that impart functionality to a device when employed as part of the device. Further examples of functional data structures include, for example, sensor data, data obtained via user input, data obtained via querying external data sources, baseline information, and so forth. The term "data structure" refers to a physical implementation of a data model's organization of data within a physical memory. As such, a data structure is formed of specific electrical or magnetic structural elements within a memory. A data structure imposes physical organization on the data stored in the memory that is used by a processor.

Device 1000 can include fewer components than those shown or include additional components other than those shown in FIG. 10 depending on the specific type of system that is implemented. Additionally, the particular operating system and/or application(s) and/or other program code included may also vary according to system type. Moreover, one or more of the illustrative components can be incorporated into, or otherwise form a portion of, another component. For example, a processor may include at least some memory.

Device 1000 is provided for purposes of illustration and not limitation. A device and/or system configured to perform the operations described herein may have a different architecture than illustrated in FIG. 10. The architecture may be a simplified version of device 1000 and may include a processor and memory storing instructions. The architecture may include one or more sensors as described herein. Device 1000, or a similar system, can collect data using the various sensors of the device or sensors coupled thereto. It should be appreciated, however, that device 1000 may include fewer sensors or other additional sensors. More generally, not all devices will include each of the components described herein. For example, earbuds will not include a camera subsystem, certain I/O devices, or other components.

Example implementations of device 1000 include, for example, a smartphone or other mobile device or phone, a wearable computing device (e.g., smartwatch, earbuds), a dedicated medical device or other suitable handheld, wearable, or comfortably carriable electronic device capable of sensing and processing sensor-detected signals and data. It will be appreciated that embodiments can be deployed as a standalone device or deployed as multiple devices in a distributed client-server networked system. For example, in certain embodiments, a mobile device (e.g., earbuds) smartwatch can operatively couple to another mobile device (e.g., smartphone). The mobile device may or may not be configured to interact with a remote server and/or computer system.

Figure 11:
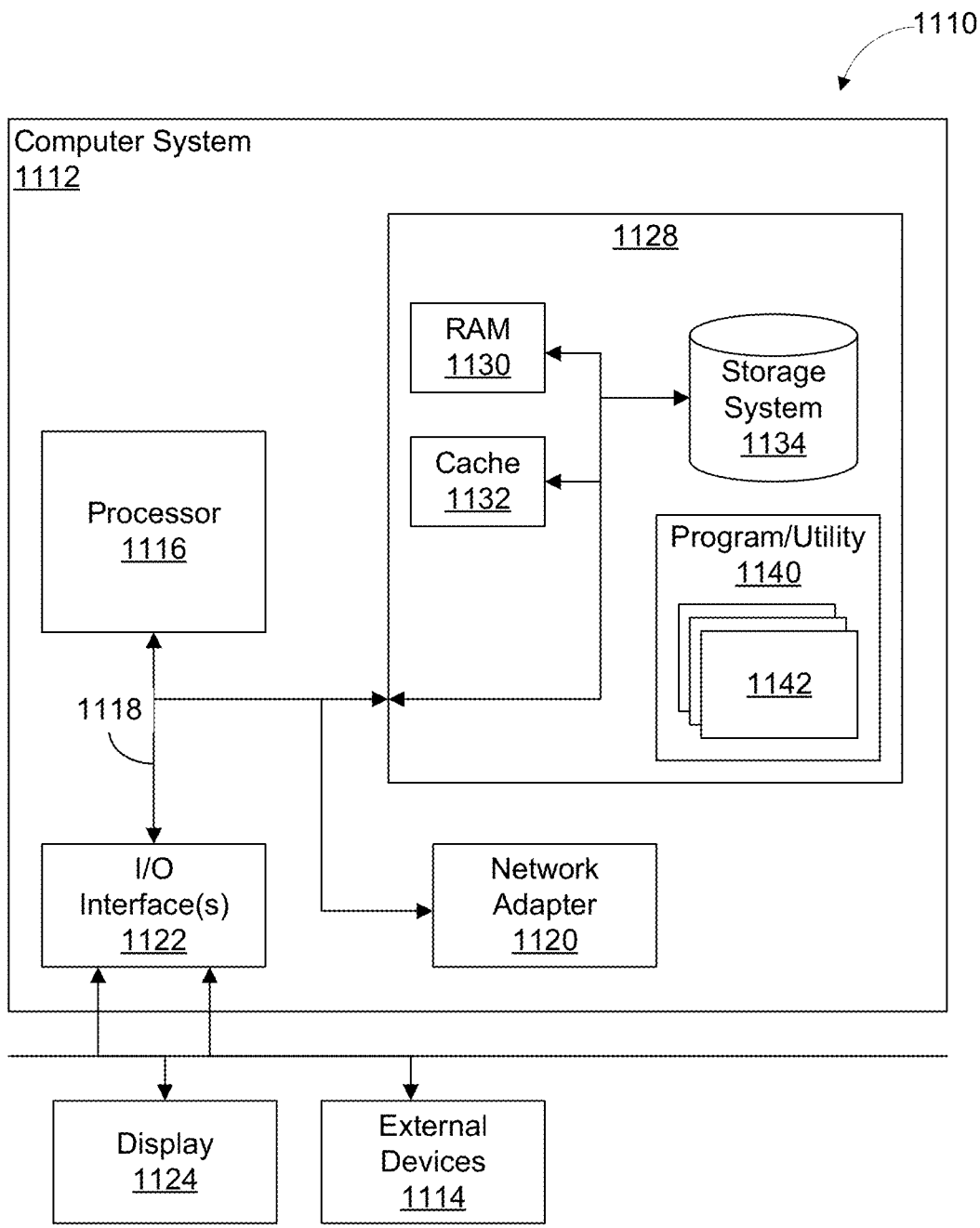
FIG. 11 illustrates an example computing node that can be used in conjunction with a device in which the system of FIG. 1 can be implemented.

FIG. 11 illustrates a schematic of an example of a computing node 1100. In one or more embodiments, computing node 1100 is an example of a cloud-based computing node (e.g., server). Computing node 1100 is not intended to suggest any limitation as to the scope of use or functionality of embodiments of the invention described herein. Computing node 1100 is capable of performing any of the functionality described within this disclosure.

Computing node 1100 includes a computer system 1112, which is operational with numerous other general-purpose or special-purpose computing system environments or configurations.

Computer system 1112 may be described in the general context of computer system-executable instructions, such as program modules, being executed by a computer system. Generally, program modules may include routines, programs, objects, components, logic, data structures, and so on that perform particular tasks or implement particular abstract data types. Computer system 1112 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 11, computer system 1112 is shown in the form of a general-purpose computing device. The components of computer system 1112 may include, but are not limited to, one or more processors 1116, a memory 1128, and a bus 1118 that couples various system components including memory 1128 to processor 1116. As defined herein, "processor" means at least one hardware circuit configured to carry out instructions. The hardware circuit may be an integrated circuit. Examples of a processor include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller.

The carrying out of instructions of a computer program by a processor comprises executing or running the program. As defined herein, "run" and "execute" comprise a series of actions or events performed by the processor in accordance with one or more machine-readable instructions. "Running" and "executing," as defined herein refer to the active performing of actions or events by the processor. The terms run, running, execute, and executing are used synonymously herein.

Bus 1118 represents one or more of any of several types of bus structures, including a memory bus or memory controller, a peripheral bus, an accelerated graphics port, and a processor or local bus using any of a variety of bus architectures. By way of example only, and not limitation, such architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus, and PCI Express (PCIe) bus.

Computer system 1112 typically includes a variety of computer system-readable media. Such media may be any available media that is accessible by computer system 1112, and may include both volatile and non-volatile media, removable and non-removable media.

Memory 1128 may include computer system readable media in the form of volatile memory, such as random-access memory (RAM) 1130 and/or cache memory 1132. Computer system 1112 may further include other removable/non-removable, volatile/non-volatile computer system storage media. By way of example, storage system 1134 can be provided for reading from and writing to a non-removable, non-volatile magnetic media and/or solid-state drive(s) (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 1118 by one or more data media interfaces. As will be further depicted and described below, memory 1128 may include at least one program product having a set (e.g., at least one) of program modules that are configured to carry out the functions of embodiments of the invention.

Program/utility 1140, having a set (at least one) of program modules 1142, may be stored in memory 1128 by way of example, and not limitation, as well as an operating system, one or more application programs, other program modules, and program data. Each of the operating system, one or more application programs, other program modules, and program data or some combination thereof, may include an implementation of a networking environment. Program modules 1142 generally carry out the functions and/or methodologies of embodiments of the invention as described herein. For example, one or more of the program modules may include code for implementing or operating in conjunction with a breathing phase detecting system the same as or similar to system 110 or portions thereof.

Program/utility 1140 is executable by processor 1116. Program/utility 1140 and any data items used, generated, and/or operated upon by computer system 1112 are functional data structures that impart functionality when employed by computer system 1112. As defined within this disclosure, a "data structure" is a physical implementation of a data model's organization of data within a physical memory. As such, a data structure is formed of specific electrical or magnetic structural elements in a memory. A data structure imposes physical organization on the data stored in the memory as used by an application program executed using a processor.

Computer system 1112 may also communicate with one or more external devices 1114 such as a keyboard, a pointing device, a display 1124, etc.; one or more devices that enable a user to interact with computer system 1112; and/or any devices (e.g., network card, modem, etc.) that enable computer system 1112 to communicate with one or more other computing devices. Such communication can occur via input/output (I/O) interfaces 1122. Still, computer system 1112 can communicate with one or more networks such as a local area network (LAN), a general wide area network (WAN), and/or a public network (e.g., the Internet) via network adapter 1120. As depicted, network adapter 1120 communicates with the other components of computer system 1112 via bus 1118. It should be understood that although not shown, other hardware and/or software components could be used in conjunction with computer system 1112. Examples, include, but are not limited to: microcode, device drivers, redundant processing units, external disk drive arrays, RAID systems, tape drives, and data archival storage systems, etc.

While computing node 1100 is used to illustrate an example of a cloud computing node, it should be appreciated that a computer system using an architecture the same as or similar to that described in connection with FIG. 11 may be used in a non-cloud computing implementation to perform the various operations described herein. In this regard, the example embodiments described herein are not intended to be limited to a cloud computing environment. Computing node 1100 is an example of a data processing system. As defined herein, "data processing system" means one or more hardware systems configured to process data, each hardware system including at least one processor programmed to initiate operations and memory.

Computing node 1100 is an example of computer hardware. Computing node 1100 may include fewer components than shown or additional components not illustrated in FIG. 11 depending upon the particular type of device and/or system that is implemented. The particular operating system and/or application(s) included may vary according to device and/or system type as may the types of I/O devices included. Further, one or more of the illustrative components may be incorporated into, or otherwise form a portion of, another component. For example, a processor may include at least some memory.

Computing node 1100 is also an example of a server. As defined herein, "server" means a data processing system configured to share services with one or more other data processing systems. As defined herein, "client device" means a data processing system that requests shared services from a server, and with which a user directly interacts. Examples of a client device include, but are not limited to, a workstation, a desktop computer, a computer terminal, a mobile computer, a laptop computer, a netbook computer, a tablet computer, a smart phone, a personal digital assistant, a smart watch, smart glasses, a gaming device, a set-top box, a smart television and the like. In one or more embodiments, the various user devices described herein may be client devices. Network infrastructure, such as routers, firewalls, switches, access points and the like, are not client devices as the term "client device" is defined herein.

The terminology used herein is for the purpose of describing particular embodiments only and is not intended to be limiting. Notwithstanding, several definitions that apply throughout this document now will be presented.

As defined herein, the singular forms "a," "an," and "the" include the plural forms as well, unless the context clearly indicates otherwise.

As defined herein, "another" means at least a second or more.

As defined herein, "at least one," "one or more," and "and/or," are open-ended expressions that are both conjunctive and disjunctive in operation unless explicitly stated otherwise. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together.

As defined herein, "automatically" means without user intervention.

As defined herein, "includes," "including," "comprises," and/or "comprising," specify the presence of stated features, integers, steps, operations, elements, and/or components, but do not preclude the presence or addition of one or more other features, integers, steps, operations, elements, components, and/or groups thereof.

As defined herein, "if" means "in response to" or "responsive to," depending upon the context. Thus, the phrase "if it is determined" may be construed to mean "in response to determining" or "responsive to determining" depending on the context. Likewise the phrase "if [a stated condition or event] is detected" may be construed to mean "upon detecting [the stated condition or event]" or "in response to detecting [the stated condition or event]" or "responsive to detecting [the stated condition or event]" depending on the context.

As defined herein, "one embodiment," "an embodiment," "in one or more embodiments," "in particular embodiments," or similar language mean that a particular feature, structure, or characteristic described in connection with the embodiment is included in at least one embodiment described within this disclosure. Thus, appearances of the aforementioned phrases and/or similar language throughout this disclosure may, but do not necessarily, all refer to the same embodiment.

As defined herein, the phrases "in response to" and "responsive to" mean responding or reacting readily to an action or event. Thus, if a second action is performed "in response to" or "responsive to" a first action, there is a causal relationship between an occurrence of the first action and an occurrence of the second action. The phrases "in response to" and "responsive to" indicate the causal relationship.

As defined herein, "real-time" means a level of processing responsiveness that a user or system senses as sufficiently immediate for a particular process or determination to be made, or that enables the processor to keep up with some external process.

As defined herein, "substantially" means that the recited characteristic, parameter, or value need not be achieved exactly, but that deviations or variations, including for example, tolerances, measurement error, measurement accuracy limitations, and other factors known to those of skill in the art, may occur in amounts that do not preclude the effect the characteristic was intended to provide.

As defined herein, the terms "individual," "subject," and "user" each refer to a human being.

The terms first, second, etc. may be used herein to describe various elements. These elements should not be limited by these terms, as these terms are only used to distinguish one element from another unless stated otherwise or the context clearly indicates otherwise.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a standalone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration and are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method of monitoring a user's breathing, the method comprising:
   passively monitoring the user's breathing with a device during a predetermined time interval thereby generating sensor-generated signals, wherein the sensor-generated signals include acoustic signals comprising audio and motion signals;
   detecting a plurality of phases of the user's breathing by processing solely the audio of the acoustic signals using a machine learning model;
   wherein the machine learning model is trained as a student model in a teacher-student architecture including a teacher model configured to teach the machine learning model by generating labels for received motion training data corresponding to human breathing, wherein the machine learning model uses the labels during a training process to learn to classify training audio corresponding to the human breathing into the plurality of phases, and wherein the training audio is time aligned with the motion training data;

identifying a breathing mode of the user's breathing and detecting that the breathing mode is a particular trigger mode selected from a plurality of detectable trigger modes including shallow breathing and mouth breathing by processing data created from the sensor-generated signals and the plurality of phases of the user's breathing using a further machine learning model trained, at least in part, to distinguish between the shallow breathing and the mouth breathing; and responsive to detecting the trigger mode, providing to the user via the device real time biofeedback specifying a breathing exercise adapted to the particular trigger mode.

2. The method of claim 1, wherein the trigger mode is the mouth breathing and the biofeedback directs the user to close a mouth of the user and breathe through a nose of the user.

3. The method of claim 1, wherein the trigger mode is the shallow breathing and the biofeedback directs the user to breathe deeply.

4. The method of claim 1, comprising:
identifying a social context corresponding to the user in which the user is engaged in a conversation based on detection of human voices; and
in response to the identifying the social context, delaying the providing of the biofeedback to the user.

5. The method of claim 1, comprising:
discarding one or more of the acoustic signals that are each identified as an unreliable signal;
wherein the identifying is based on a comparison of the plurality of phases of the user's breathing.

6. The method of claim 1, comprising:
providing the biofeedback to the user via the device based on the plurality of phases of the user's breathing as the user performs the breathing exercise.

7. The method of claim 1, comprising:
identifying a breathing pattern of the user based on the plurality of phases of the user's breathing;
comparing the breathing pattern identified with a target pattern specified in response to user input to the device; and
generating an instruction based on the comparing and conveying the instruction to the user with the device.

8. The method of claim 1, comprising:
identifying a breathing pattern of the user based on the plurality of phases of the user's breathing;
detecting in real time a corresponding physiological condition of the user; and
generating an instruction, based on the breathing pattern and the corresponding physiological condition, and conveying the instruction to the user with the device.

9. A system, comprising:
a processor configured to initiate operations including:
passively monitoring a user's breathing with a device during a predetermined time interval thereby generating sensor-generated signals, wherein the sensor-generated signals include acoustic signals comprising audio and motion signals;
detecting a plurality of phases of the user's breathing by processing solely the audio of the acoustic signals using a machine learning model;
wherein the machine learning model is trained as a student model in a teacher-student architecture including a teacher model configured to teach the machine learning model by generating labels for received motion training data corresponding to human breathing, wherein the machine learning model uses the labels during a training process to learn to classify training audio corresponding to the human breathing into the plurality of phases, and wherein the training audio is time aligned with the motion training data;

identifying a breathing mode of the user's breathing and detecting that the breathing mode is a particular trigger mode selected from a plurality of detectable trigger modes including shallow breathing and mouth breathing by processing data created from the sensor-generated signals and the plurality of phases of the user's breathing using a further machine learning model trained, at least in part, to distinguish between the shallow breathing and the mouth breathing; and responsive to detecting the trigger mode, providing to the user via the device real time biofeedback specifying a breathing exercise adapted to the particular trigger mode.

10. The system of claim 9, wherein the trigger mode is the mouth breathing and the biofeedback directs the user to close a mouth of the user and breathe through a nose of the user.

11. The system of claim 9, wherein the trigger mode is the shallow breathing and the biofeedback directs the user to breathe deeply.

12. The system of claim 9, wherein the processor is configured to initiate further operations including:
identifying a social context corresponding to the user in which the user is engaged in a conversation based on detection of human voices; and
in response to the identifying the social context, delaying the providing of the biofeedback.

13. The system of claim 9, wherein the processor is configured to initiate further operations including:
discarding one or more of the acoustic signals that are each identified as an unreliable signal;
wherein the identifying is based on a comparison of the plurality of phases of the user's breathing.

14. The system of claim 9, wherein the processor is configured to initiate further operations including:
providing biofeedback to the user via the device based on the plurality of phases of the user's breathing as the user performs the breathing exercise.

15. The system of claim 9, wherein the processor is configured to initiate further operations including:
identifying a breathing pattern of the user based on the plurality of phases of the user's breathing;
comparing the breathing pattern identified with a target pattern specified in response to user input to the device; and
generating an instruction based on the comparing and conveying the instruction to the user with the device.

16. The system of claim 9, wherein the processor is configured to initiate further operations including:
identifying a breathing pattern of the user based on the plurality of phases of the user's breathing;
detecting in real time a corresponding physiological condition of the user; and
generating an instruction, based on the breathing pattern and the corresponding physiological condition, and conveying the instruction to the user with the device.

17. A method of monitoring a user's breathing, the method comprising:

training a first machine learning model as a student model in a teacher-student architecture to detect a plurality of breathing phases by:
  generating labels corresponding to the plurality of breathing phases using a teacher model configured to operate on motion training data corresponding to human breathing;
  teaching the first machine learning model to classify training audio into the plurality of breathing phases based on the labels from the teacher model, wherein the training audio corresponds to the human breathing and is time aligned with the motion training data;
passively monitoring the user's breathing by detecting audio with an acoustic sensor of a device; and
classifying the breathing of the user into the plurality of breathing phases by processing solely the audio monitored by the acoustic sensor using the first machine learning model as trained.

18. The method of claim 17, further comprising:
identifying a breathing mode of the user's breathing by processing the plurality of breathing phases of the breathing of the user through a second machine learning model; and
in response to detecting that the breathing mode is a trigger mode, generating an instruction adapted to the trigger mode and conveying the instruction to the user via the device.

\* \* \* \* \*